US006194418B1

(12) United States Patent
Seitz et al.

(10) Patent No.: US 6,194,418 B1
(45) Date of Patent: Feb. 27, 2001

(54) SUBSTITUTED AMINOSALICYCLIC ACID AMIDES WITH FUNGICIDAL EFFECT AND INTERMEDIATE PRODUCTS FOR PRODUCTION THEREOF

(75) Inventors: Thomas Seitz, Langenfeld; Uwe Stelzer, Burscheid; Peter Wolfrum, Monheim; Klaus Stenzel, Düsseldorf, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/380,969

(22) PCT Filed: Mar. 2, 1998

(86) PCT No.: PCT/EP98/01164

§ 371 Date: Sep. 13, 1999

§ 102(e) Date: Sep. 13, 1999

(87) PCT Pub. No.: WO98/41513

PCT Pub. Date: Sep. 24, 1998

(30) Foreign Application Priority Data

Mar. 14, 1997 (DE) ............................................. 197 10 609

(51) Int. Cl.$^7$ ........................ A61K 31/505; A61K 31/44; A61K 31/41; C07D 333/22; C07C 233/00
(52) U.S. Cl. ........................ 514/256; 514/356; 514/363; 514/438; 514/619; 544/335; 546/336; 549/77; 564/168
(58) Field of Search ............................... 564/168; 514/619, 514/356, 256, 438, 363; 546/336; 544/335; 549/77; 548/136

(56) References Cited

U.S. PATENT DOCUMENTS

| | | | |
|---|---|---|---|
| 3,527,865 | 9/1970 | Taborsky | 424/230 |
| 4,762,830 | 8/1988 | Sturm et al. | 514/270 |
| 5,679,676 | 10/1997 | Kruger et al. | 514/229.2 |
| 5,883,250 | 3/1999 | Kruger et al. | 540/544 |
| 6,001,879 | 12/1999 | Seitz et al. | 514/616 |

FOREIGN PATENT DOCUMENTS

| | | |
|---|---|---|
| 2210861 | 11/1972 | (DE) . |
| 0 382 375 | 8/1990 | (EP) . |
| 0 463 488 | 1/1992 | (EP) . |
| 0 920 867 | 6/1999 | (EP) . |
| 1356391 | 6/1974 | (GB) . |
| 61-205262 | 9/1986 | (JP) . |
| 92/18487 | 10/1992 | (WO) . |
| 94/02470 | 2/1994 | (WO) . |
| 95/14674 | 6/1995 | (WO) . |
| 95/24383 | 9/1995 | (WO) . |

OTHER PUBLICATIONS

J. Med. Chem. 33, 136 (1990).
Biochim. Biophys. Acta 1141, 262 (1993).
J. Med. Chem. 39, 1521 (1996).
Chemical Abstract: 106:84632, 1995.
Pharm. Chem. J., 23, (Engl. Translation from Khimoiko–farmatsevticheskii Zhurnal, vol. 23, No. 6, pp. 705–707, Jun. 1989, P.I. Vainilavichyus et al, pp. 500–503 (month unavailablel) 1989, Synthesis and Biological Activity of Ethyl (6–Phenoxy–4–Pyrimidinylthio)Acetates.
J. Am. Chem. Soc., Oct. 5, 1959, pp. 5215–5217, Okumura et al.
J. Chem. Soc. (month unavailable) 1955, Chesterfield et al, pp. 3478–3481, Pyrimidines, Part VIII, Halogeno– and Hydrazino–pyrimidines.

*Primary Examiner*—Deborah C. Lambkin
(74) *Attorney, Agent, or Firm*—Joseph C. Gil

(57) ABSTRACT

The invention relates to novel substituted aminosalicylamides, to a plurality of processes for their preparation and to their use as fungicides, and also to novel intermediates and to a plurality of processes for their preparation.

18 Claims, No Drawings

SUBSTITUTED AMINOSALICYCLIC ACID AMIDES WITH FUNGICIDAL EFFECT AND INTERMEDIATE PRODUCTS FOR PRODUCTION THEREOF

This application is a 371 of PCT/EP98/01164 Feb. 2, 1998.

The invention relates to novel substituted aminosalicylic acid amides with fungicidal effect and intermediate products for production thereof, to a plurality of processes for their preparation and to their use as fungicides, and also to novel intermediates and to a plurality of processes for their preparation.

Certain substituted acylaminosalicylamides, such as, for example, the compounds 3-formamido-salicylanilide and 3-(formylamino)-2-hydroxy-N-(phenylmethyl)-benzamide, are already known (compare, for example, Biochim. Biophys. Acta (1993), 1142(3), 262–8, J. Med. Chem. (1990), 33(1), 136–42 or J. Biol. Chem. (1971), 246(23), 7125–30). However, a pesticidal activity of these prior-art compounds has hitherto not been described.

The present invention, accordingly, provides the novel substituted aminosalicylamides of the general formula (I),

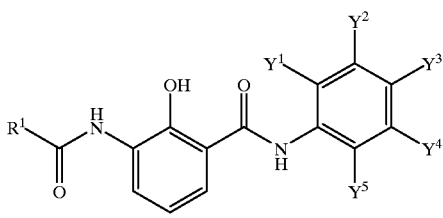

(I)

in which
$R^1$ represents hydrogen, alkyl or alkoxy,
$Y^1$, $Y^2$, $Y^3$, $Y^4$ and $Y^5$ are identical or different and each represents hydrogen, halogen, cyano, alkyl, halogenoalkyl, alkoxy or halogenoalkoxy, and either $Y^2$ or $Y^3$ represents —G—Z, in which
G represents one of the groupings below
—Q—CQ—, —CQ—Q—, —CQ—Q—CH$_2$—, —CH$_2$—Q—CQ—, —Q—CQ—CH$_2$—, —QCQ—Q—CH$_2$—, N=N, —S(O)$_n$—, —CH$_2$—S(O)$_n$—, —CQ—, —S(O)$_n$—CH$_2$—, —C(R$^3$)=N—O—, —C(R$^3$)=N—O—CH$_2$—, —N(R$^4$)—, —CQ—N(R$^4$)—, —N(R$^4$)—CQ—, —Q—CQ—N(R$^4$)—, —N=C(R$^3$)—Q—CH$_2$—, —CH$_2$—O—N=C(R$^3$)—, —C(CH$_3$)—O—N=C(R$^3$)—, —N(R$^4$)—CQ—Q—, —CQ—N(R$^4$)—CQ—Q—, —N(R$^4$)—CQ—Q—CH$_2$—, —Q—C(R$^3$)=N—O—CH$_2$—, —N(R$^4$)—C(R$^3$)=N—O—CH$_2$—, —O—CH$_2$—C(R$^3$)=N—O—CH$_2$—, —N=N—C(R$^3$)=N—O—CH$_2$—, —C(=N—O—R$^5$)—C(R$^3$)=N—O—CH$_2$—, —C(=N—O—R$^5$)—C(R$^3$)—O—N=CH—, —C(=N—O—R$^5$)—C(R$^3$)—O—N=C(CH$_3$)—, —T—Ar$^1$—or —T—Ar$^1$—Q—, where
Ar$^1$ represents optionally substituted arylene, heteroarylene, cycloalkylene or heterocycloalkylene (i.e. a doubly attached aliphatic ring in which one or more carbon atoms are replaced by heteroatoms, i.e. by atoms different from carbon),
n represents the numbers 0, 1 or 2,
Q represents oxygen or sulphur,
$R^3$ represents hydrogen, cyano or in each case optionally substituted alkyl, alkoxy, alkylthio, alkylamino, dialkylamino or cycloalkyl, and $R^4$ represents hydrogen, hydroxyl, cyano or in each case optionally substituted alkyl, alkoxy or cycloalkyl,
$R^5$ represents hydrogen or alkyl and
T represents a single bond, represents oxygen, sulphur, —CH$_2$—O—, —CH$_2$—S— or represents optionally substituted alkanediyl,
Z represents in each case optionally substituted alkyl, alkenyl, alkinyl, cycloalkyl, aryl or heterocyclyl.

In the definitions, the hydrocarbon chains, such as alkyl, alkylene, alkenyl or alkinyl, are in each case straight-chain or branched, including in combination with heteroatoms, such as an alkoxy, alkylthio or alkylamino.

Halogen generally represents fluorine, chlorine, bromine or iodine, preferably fluorine, chlorine or bromine, in particular fluorine or chlorine.

Aryl represents aromatic, mono or polycyclic hydrocarbon rings, such as, for example, phenyl, naphthyl, anthranyl, phenanthryl, preferably phenyl or naphthyl, in particular phenyl.

Heterocyclyl represents saturated or unsaturated, and also aromatic, cyclic compounds having up to eight ring members in which at least one ring member is a heteroatom, i.e. an atom different from carbon. If the ring contains a plurality of heteroatoms, these can be identical or different. Preferred heteroatoms are oxygen, nitrogen or sulphur. If appropriate, the cyclic compounds form, together with further carbocyclic or heterocyclic, fused-on or bridged rings, a polycyclic ring system. Preference is given to mono- or bicyclic ring systems, in particular to mono- or bicyclic aromatic ring systems.

Cycloalkyl represents saturated carbocyclic cyclic compounds which form, if appropriate, a polycyclic ring system with other carbocyclic fused-on or bridged rings.

Cycloalkenyl represents carbocyclic cyclic compounds which contain at least one double bond and which form, if appropriate, a polycyclic ring system with other carbocyclic fused-on or bridged rings.

Furthermore, it has been found that the novel substituted acylamino-salicylamides of the general formula (I) are obtained when
a) aminosalicylamides of the general formula (II),

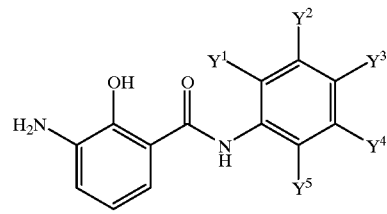

(II)

in which
$Y^1$, $Y^2$, $Y^3$, $Y^4$ and $Y^5$ are each as defined above, are reacted with acylating agents of the general formula (III),

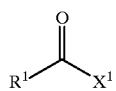

(III)

in which
$R^1$ is as defined above and $X^1$ represents halogen, hydroxyl, alkoxy or alkylcarbonyloxy, if appropriate in the presence of a diluent, if appropriate in the presence of an acid acceptor, and if appropriate in the presence of a further reaction auxiliary, or when b) nitrosalicylamides of the general formula (IV)

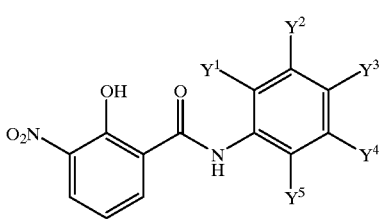

(IV)

in which $Y^1$, $Y^2$, $Y^3$, $Y^4$ and $Y^5$ are each as defined above are reacted with formic acid, if appropriate in the presence of a catalyst and if appropriate in the presence of a further reaction auxiliary, or when c) O-benzyl-nitrosalicylamides of the general formula (V),

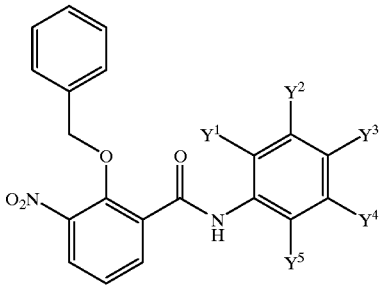

(V)

in which $Y^1$, $Y^2$, $Y^3$, $Y^4$ and $Y^5$ are each as defined above, are reacted with formic acid, if appropriate in the presence of hydrogen or a base metal, if appropriate in the presence of a catalyst and if appropriate in the presence of a further reaction auxiliary.

Finally, it has been found that the novel substituted aminosalicylamides of the general formula (I) have very strong fungicidal activity.

If appropriate, the compounds according to the invention and their precursors are present as mixtures of various possible isomeric forms, in particular of stereoisomers, such as, for example, E and Z, threo and erythro, and also optical isomers or else tautomers. What is claimed are both the E and the Z isomers, and also the threo and erythro and the optical isomers, and also the possible tautomers, and any mixtures of these isomers.

In the general formula (I), $R^1$ preferably represents hydrogen, alkyl having 1 to 4 carbon atoms or alkoxy having 1 to 4 carbon atoms;
in particular represents hydrogen, methyl, ethyl, n- or i-propyl, methoxy or ethoxy; preferably hydrogen, methyl or methoxy; particularly preferably hydrogen.

In the general formula (I), $Y^1$, $Y^4$ and $Y^5$ independently of one another each preferably represents hydrogen, halogen, cyano, alkyl or alkoxy having in each case 1 to 4 carbon atoms, halogenoalkyl, or halogenoalkoxy having in each case 1 to 4 carbon atoms; in particular represents hydrogen, fluorine, chlorine, bromine, cyano, methyl, ethyl, methoxy, trifluoromethyl or difluoromethoxy; preferably hydrogen.

In the general formula (I), $Y^2$ and $Y^3$ independently of one another each preferably represents hydrogen, halogen, cyano, alkyl or alkoxy having in each case 1 to 4 carbon atoms, halogenoalkyl, or halogenoalkoxy having in each case 1 to 4 carbon atoms and 1 to 5 identical or different halogen atoms and one of the radicals $Y^2$ or $Y^3$ represents the group —G—Z.

In particular, $Y^2$ represents hydrogen, fluorine, chlorine, bromine, cyano, methyl, ethyl, methoxy, trifluoromethyl or difluoromethoxy; preferably hydrogen.

In particular, $Y^3$ represents hydrogen, fluorine, chlorine, bromine, cyano, methyl, ethyl, methoxy, trifluoromethyl or difluoromethoxy; preferably the group —G—Z.

In the general formula (I), G preferably represents one of the groupings below

—Q—CQ—, —CQ—Q—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$—, —CQ—, —S(O)$_n$—CH$_2$—, —C(R$^3$)=N—O—, —C(R$^3$)=N—O—CH$_2$—, —N(R$^4$)—, —CQ—N(R$^4$)—, —N(R$^4$)—CQ—, —Q—CQ—N(R$^4$)—, —N=C(R$^3$)—Q—CH$_2$—, —CH$_2$—O—N=C(R$^3$)—, —C(CH$_3$)—O—N=C(R$^3$)—, —N(R$^4$)—CQ—Q—, —CQ—N(R$^4$)—CQ—Q—, —N(R$^4$)—CQ—Q—CH$_2$—, —Q—C(R$^3$)=N—O—CH$_2$—, —N(R$^4$)—C(R$^3$)=N—O—CH$_2$—, —O—CH$_2$—C(R$^3$)=N—O—CH$_2$—, —N=N—C(R$^3$)=N—O—CH$_2$—, —C(=N—O—R$^5$)—C(R$^3$)=N—O—CH$_2$—, —C(=N—O—R$^5$)—C(R$^3$)—O—N=CH—, —C(=N—O—R$^5$)—C(R$^3$)—O—N=C(CH$_3$)—, —T—Ar$^1$— or —T—Ar$^1$—Q—;

where Q, n, $R^3$, $R^4$ and $R^5$ are each as defined in the application.

In particular, G represents —C(R$^3$)=N—O—CH$_2$—, where $R^3$ preferably represents cyclopropyl and in particular methyl.

G preferably represents —T—Ar$^1$—, —T—Ar$^1$—S— and in particular —T—Ar$^1$—O—, where T preferably represents a single bond, represents oxygen, sulphur, —CH$_2$—O—, —CH$_2$—S— or represents alkanediyl having 1 to 3 carbon atoms, in particular represents a single bond, represents oxygen, sulphur, —CH$_2$—O—, —CH$_2$—S—, methylene, ethylene or propylene and preferably oxygen.

Ar$^1$ preferably represents phenylene, naphthylene, cycloalkylene, each of which is optionally mono- or polysubstituted by identical or different substituents, or represents heteroarylene or heterocycloalkylene having 3 to 7 ring members, at least one of which represents oxygen, sulphur or nitrogen and one or two more optionally represent nitrogen, where the possible substituents are preferably selected from the list below:
halogen, cyano, amino, hydroxyl, formyl, carboxyl, carbamoyl, thiocarbamoyl;
in each case straight-chain or branched alkyl, alkoxy, alkylthio, alkylsulphinyl or alkylsulphonyl having in each case 1 to 6 carbon atoms;
in each case straight-chain or branched alkenyl or alkenyloxy having in each case 2 to 6 carbon atoms;
in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 11 identical or different halogen atoms;

in each case straight-chain or branched alkylamino, dialkylamino, alkylcarbonyl, alkylcarbonyloxy, alkoxycarbonyl, alkylsulphonyloxy, hydroximinoalkyl or alkoxyiminoalkyl having in each case 1 to 6 carbon atoms in the individual alkyl moieties, and also cycloalkyl having 3 to 6 carbon atoms and $Ar^1$ in particular represents phenylene or pyridinediyl, each of which is optionally mono- to trisubstituted by identical or different substituents, represents in each case optionally monosubstituted pyrimidinediyl, pyridazinedlyl, pyrazinediyl, 1,2,3-triazinediyl, 1,2,4-triazinediyl or 1,3,5-triazinediyl or represents 1,2,4-thiadiazolediyl, 1,3,4-thiadiazolediyl, 1,2,4-oxadiazolediyl, 1,3,4-oxadiazolediyl, where the possible substituents are preferably selected from the list below:

fluorine, chlorine, bromine, cyano, methyl, ethyl, n- or i-propyl, n-,i-,s- or t-butyl, cyclopropyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl and $Ar^1$ preferably represents 1,3,4-thiadiazolediyl, 1,2,4-oxadiazolediyl, 1,3,4-oxadiazolediyl or represents pyridinediyl, pyrimidinediyl or 1,3,5-triazinediyl, each of which is optionally mono- or disubstituted by identical or different substituents, possible substituents being the substituents mentioned above, or particularly preferably represents 1,2,4-thiadiazolediyl or pyrimidinediyl which is optionally mono- or disubstituted by identical or different substituents, possible substituents being those mentioned above, where the substituents preferably represent halogen, in particular fluorine.

In the general formula (I),

Z preferably represents alkyl having 1 to 8 carbon atoms which is optionally mono- or polysubstituted by identical or different substituents selected from the group consisting of halogen, cyano, hydroxyl, amino, $C_1$–$C_4$-alkoxy, $C_1$–$C_4$-alkylthio, $C_1$–$C_4$-alkylsulphinyl and $C_1$–$C_4$-alkylsulphonyl (each of which may optionally be substituted by halogen);

represents in each case optionally halogen-substituted alkenyl or alkinyl having in each case up to 8 carbon atoms;

represents cycloalkyl having 3 to 6 carbon atoms which is in each case optionally mono- or polysubstituted by identical or different substituents selected from the group consisting of halogen, cyano, carboxyl, phenyl (which is optionally substituted by halogen, cyano, $C_1$–$C_4$-alkyl, $C_1$–$C_4$-halogenoalkyl, $C_1$–$C_4$-alkoxy or $C_1$–$C_4$-halogenoalkoxy), $C_1$–$C_4$-alkyl and $C_1$–$C_4$-alkoxy-carbonyl;

represents phenyl, naphthyl, each of which is optionally mono- or polysubstituted by identical or different substituents, or represents heterocyclyl having 3 to 7 ring members, at least one of which represents oxygen, sulphur or nitrogen and one or two more optionally represent nitrogen, where the possible substituents are preferably selected from the list below:

halogen, cyano, amino, hydroxyl, formyl, carboxyl, carbamoyl, thiocarbamoyl;

in each case straight-chain or branched alkyl, alkoxy, alkylthio, alkylsulphinyl or alkylsulphonyl having in each case 1 to 6 carbon atoms;

in each case straight-chain or branched alkenyl or alkenyloxy having in each case 2 to 6 carbon atoms;

in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 11 identical or different halogen atoms;

in each case straight-chain or branched alkylamino, dialkylamino, alkylcarbonyl, alkylcarbonyloxy, alkoxycarbonyl or alkylsulphonyloxy, having in each case 1 to 6 carbon atoms in the individual alkyl moieties;

in each case doubly attached alkylene or dioxyalkylene having in each case 1 to 6 carbon atoms and being in each case optionally mono- or polysubstituted by identical or different substituents selected from the group consisting of halogen, straight-chain or branched alkyl having 1 to 4 carbon atoms and straight-chain or branched halogenoalkyl having 1 to 4 carbon atoms and 1 to 9 identical or different halogen atoms;

cycloalkyl having 3 to 6 carbon atoms;

phenyl or phenoxy, each of which is mono- or polysubstituted by identical or different substituents selected from the group consisting of halogen and straight-chain or branched alkyl having 1 to 4 carbon atoms;

heterocyclyl or heterocyclyl-methyl having in each case 3 to 7 ring members, 1 to 3 of which are in each case identical or different heteroatoms—in particular nitrogen, oxygen and/or sulphur—, or a grouping 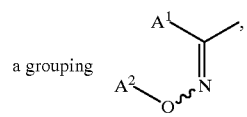

in which $A^1$ represents alkyl having 1 to 4 carbon atoms or cycloalkyl having 1 to 6 carbon atoms and $A^2$ represents optionally cyano-, alkoxy-, alkylthio-, alkylamino-, dialkylamino- or phenyl-substituted alkyl having 1 to 4 carbon atoms, alkenyl or alkinyl having in each case 2 to 4 carbon atoms, or a grouping 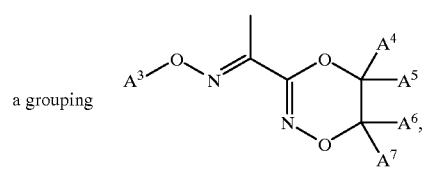

in which $A^3$ represents alkyl having 1 to 4 carbon atoms and $A^4$, $A^5$, $A^6$ and $A^7$ are identical or different and, independently of one another, each represents hydrogen, alkyl or hydroxyalkyl having in each case 1 to 4 carbon atoms or halogenoalkyl having 1 to 4 carbon atoms and 1 to five identical or different halogen atoms, or $A^4$ and $A^5$ or $A^4$ and $A^6$ or $A^6$ and $A^7$ together with the respective carbon atoms to which they are attached form a cycloaliphatic ring having five, six or seven carbon atoms.

In the general formula (I),

Z in particular represents methyl, ethyl, n- or i-propyl, n-, i-, s- or t-butyl which is optionally mono- to trisubstituted by identical or different substituents selected from the group consisting of fluorine, chlorine, cyano and methoxy;

represents in each case optionally fluorine- or chlorine-substituted vinyl, allyl or propargyl;

represents cyclopropyl, cyclobutyl, cyclopentyl or cyclohexyl, each of which is optionally mono- to trisubstituted by identical or different substituents selected from the group consisting of fluorine, chlorine, cyano, methoxy, phenyl, methyl or ethyl;

and preferably represents phenyl, 1,2,4-thiadiazolyl, 1,3,4-thiadiazolyl, 1,2,4-oxadiazolyl, 1,3,4-oxadiazolyl, pyridinyl, pyrimidyl, pyridazinyl, pyrazinyl, 1,2,3-triazinyl, 1,2,4-triazinyl or 1,3,5-triazinyl, each of which is optionally mono- to trisubstituted by identical or different substituents, where the possible substituents are each as defined above and preferably selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, in each case doubly attached methylenedioxy, ethylenedioxy, each of which is optionally mono- to tetrasubstituted by identical or different substituents selected from the group consisting of fluorine, chlorine, methyl, trifluoromethyl and ethyl, phenyl, 4-chlorophenyl, 4-methylphenyl, phenoxy, 4-chlorophenoxy, 4-methylphenoxy, cyclopropyl, cyclobutyl, cyclopentyl or cyclohexyl, or a grouping 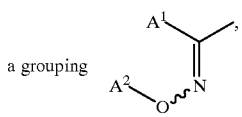

in which $A^1$ represents methyl, ethyl, n- or i-propyl, n-, i-, s- or t-butyl, cyclopropyl or cyclobutyl, $A^2$ represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl, or a grouping 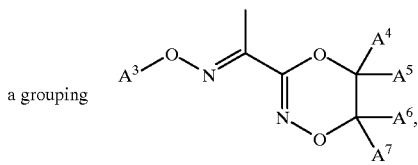

in which $A^3$ represents methyl or ethyl and $A^4$, $A^5$, $A^6$ and $A^7$ are identical or different and independently of one another each represents hydrogen, methyl, ethyl, n- or i-propyl, n-, i-, s- or t-butyl, hydroxymethyl, trifluoromethyl or trifluoroethyl, or $A^4$ and $A^5$ or $A^4$ and $A^6$ or $A^6$ and $A^7$ together with the respective carbon atoms to which they are attached form a cycloaliphatic ring having five, six or seven carbon atoms.

In the general formula (I),

Z preferably represents methyl, ethyl, n- or i-propyl, n-, i-, s- or t-butyl, which is optionally mono- to trisubstituted by identical or different substituents selected from the group consisting of fluorine, chlorine, cyano or methoxy;

represents in each case optionally fluorine- or chlorine-substituted vinyl, allyl or propargyl;

represents cyclopropyl, cyclobutyl, cyclopentyl or cyclohexyl, each of which is optionally mono- to trisubstituted by identical or different substituents selected from the group consisting of fluorine, chlorine, cyano, methoxy, phenyl, methyl or ethyl;

and preferably represents phenyl, pyridyl, pyrimidyl or thienyl, each of which is optionally mono- to trisubstituted by identical or different substituents, where the possible substituents are as defined above and preferably selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl, trifluoromethylsulphonyl, methoxycarbonyl, ethoxycarbonyl or phenoxy;

in each case doubly attached methylenedioxy, ethylenedioxy, each of which is optionally mono- to tetrasubstituted by identical or different substituents selected from the group consisting of fluorine, chlorine, methyl, trifluoromethyl and ethyl;

cyclopropyl, cyclobutyl, cyclopentyl, cyclohexyl, phenyl, phenoxy, or a grouping 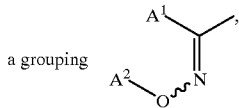

in which $A^1$ represents methyl, ethyl, n- or i-propyl, n-, i-, s- or t-butyl, cyclopropyl or cyclobutyl, $A^2$ represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl, or a grouping 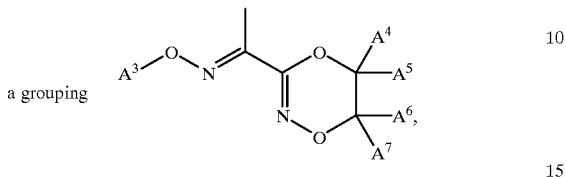

in which
A$^3$ represents methyl or ethyl and
A$^4$, A$^5$, A$^6$ and A$^7$ are identical or different and independently of one another each represents hydrogen, methyl, ethyl, n- or i-propyl, n-, i-, s- or t-butyl, hydroxymethyl, trifluoromethyl or trifluoroethyl, or
A$^4$ and A$^5$ or A$^4$ and A$^6$ or A$^6$ and A$^7$ together with the respective carbon atoms to which they are attached form a cycloaliphatic ring having five, six or seven carbon atoms.

In the general formula (I),
Z particularly preferably represents pyridyl, pyrimidyl, each of which is optionally mono- to trisubstituted by identical or different substituents, and in particular represents phenyl which is unsubstituted or mono- to trisubstituted by identical or different substituents, where the possible substituents are as defined above and preferably selected from the list below:
fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl, trifluoromethylsulphonyl, methoxycarbonyl, ethoxycarbonyl or phenoxy;
the present application preferably provides aminosalicylamides of the formula (I) in which
R$^1$ represents hydrogen, alkyl having 1 to 4 carbon atoms or alkoxy having 1 to 4 carbon atoms,
Y$^1$, Y$^2$, Y$^3$, Y$^4$ and Y$^5$ are identical or different and each represents hydrogen, halogen, cyano, alkyl or alkoxy having in each case 1 to 4 carbon atoms, halogenoalkyl, or halogenoalkoxy having in each case 1 to 4 carbon atoms and 1 to 5 identical or different halogen atoms, and either
Y$^2$ or Y$^3$ represents —G—Z, in which
G represents one of the groupings below
—Q—CQ—, —CQ—Q—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$—, —CQ—, —S(O)$_n$—CH$_2$—, —C(R$^3$)=N—O—, —C(R$^3$)=N—O—CH$_2$—, —N(R$^4$)—, —CQ—N(R$^4$)—, —N(R$^4$)—CQ—, —Q—CQ—N(R$^4$)—, —N=C(R$^3$)—Q—CH$_2$—, —CH$_2$—O—N=C(R$^3$)—, —C(CH$_3$)—O—N=C(R$^3$)—, —N(R$^4$)—CQ—Q—, —CQ—N(R$^4$)—CQ—Q—, —N(R$^4$)—CQ—Q—CH$_2$—, —Q—C(R$^3$)=N—O—CH$_2$—, —N(R$^4$)—C(R$^3$)=N—O—CH$_2$—, —O—CH$_2$—C(R$^3$)=N—O—CH$_2$—, —N=N—C(R$^3$)=N—O—CH$_2$—, —C(=N—O—R$^5$)—C(R$^3$)=N—O—CH$_2$—, —C(=N—O—R$^5$)—C(R$^3$)—O—N=CH—, —C(=N—O—R$^5$)—C(R$^3$)—O—N=C(CH$_3$)—, —T—Ar$^1$— or —T—Ar$^1$—Q—, where
n represents the numbers 0, 1 or 2,
Q represents oxygen or sulphur,
R$^3$ represents hydrogen, cyano, represents in each case optionally halogen-, cyano- or C$_1$–C$_4$-alkoxy-substituted alkyl, alkoxy, alkylthio, alkylamino or dialkylamino having in each case 1 to 6 carbon atoms in the alkyl groups or represents in each case optionally halogen-, cyano-, carboxyl-, C$_1$–C$_4$-alkyl- or C$_1$–C$_4$-alkoxy-carbonyl-substituted cycloalkyl having 3 to 6 carbon atoms, and
R$^4$ represents hydrogen, hydroxyl, cyano or represents optionally halogen-, cyano- or C$_1$–C$_4$-alkoxy-substituted alkyl having 1 to 6 carbon atoms or represents optionally halogen-, cyano-, carboxyl-, C$_1$–C$_4$-alkyl- or C$_1$–C$_4$-alkoxy-carbonyl-substituted cycloalkyl having 3 to 6 carbon atoms,
R$^5$ represents hydrogen or alkyl having 1 to 4 carbon atoms,
Ar$^1$ represents phenylene, naphthylene or cycloalkylene, each of which is optionally mono- or polysubstituted by identical or different substituents, or represents heteroarylene or heterocycloalkylene having 3 to 7 ring members, at least one of which represents oxygen, sulphur or nitrogen and one or two more optionally represent nitrogen, where the possible substituents are preferably selected from the list below:
halogen, cyano, amino, hydroxyl, formyl, carboxyl, carbamoyl, thiocarbamoyl;
in each case straight-chain or branched alkyl, alkoxy, alkylthio, alkylsulphinyl or alkylsulphonyl having in each case 1 to 6 carbon atoms;
in each case straight-chain or branched alkenyl or alkenyloxy having in each case 2 to 6 carbon atoms;
in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;
in each case straight-chain or branched halogenoalkenyl or halogenoalkenyloxy having in each case 2 to 6 carbon atoms and 1 to 11 identical or different halogen atoms;
in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties, and also
cycloalkyl having 3 to 6 carbon atoms and
T represents a single bond, represents oxygen, sulphur, —CH$_2$—O—, —CH$_2$—S— or represents alkanediyl having 1 to 3 carbon atoms,
Z represents alkyl having 1 to 8 carbon atoms which is optionally mono- or polysubstituted by identical or different substituents selected from the group consisting of halogen, cyano, hydroxyl, amino, C$_1$–C$_4$-alkoxy, $C_1$–$C_4$-alkylthio, $C_1$–$C_4$-alkylsulphinyl and $C_1$–$C_4$-alkylsulphonyl (each of which may optionally be substituted by halogen);

represents in each case optionally halogen-substituted alkenyl or alkinyl having in each case up to 8 carbon atoms;

represents cycloalkyl having 3 to 6 carbon atoms which is in each case optionally mono- or polysubstituted by identical or different substituents selected from the group consisting of halogen, cyano, carboxyl, phenyl (which is optionally substituted by halogen, cyano, $C_1$–$C_4$-alkyl, $C_1$–$C_4$-halogenoalkyl, $C_1$–$C_4$-alkoxy or $C_1$–$C_4$-halogenoalkoxy), $C_1$–$C_4$-alkyl and $C_1$–$C_4$-alkoxy-carbonyl;

represents phenyl, naphthyl, each of which is optionally mono- or polysubstituted by identical or different substituents, or represents heterocyclyl having 3 to 7 ring members, at least one of which represents oxygen, sulphur or nitrogen and one or two more optionally represent nitrogen, where the possible substituents are preferably selected from the list below:

halogen, cyano, amino, hydroxyl, formyl, carboxyl, carbamoyl, thiocarbamoyl;

in each case straight-chain or branched alkyl, alkoxy, alkylthio, alkylsulphinyl or alkylsulphonyl having in each case 1 to 6 carbon atoms;

in each case straight-chain or branched alkenyl or alkenyloxy having in each case 2 to 6 carbon atoms;

in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 11 identical or different halogen atoms;

in each case straight-chain or branched alkylamino, dialkylamino, alkylcarbonyl, alkylcarbonyloxy, alkoxycarbonyl or alkylsulphonyloxy, having in each case 1 to 6 carbon atoms in the individual alkyl moieties;

in each case doubly attached alkylene or dioxyalkylene having in each case 1 to 6 carbon atoms and being in each case optionally mono- or polysubstituted by identical or different substituents selected from the group consisting of halogen, straight-chain or branched alkyl having 1 to 4 carbon atoms and straight-chain or branched halogenoalkyl having 1 to 4 carbon atoms and 1 to 9 identical or different halogen atoms;

cycloalkyl having 3 to 6 carbon atoms;

phenyl or phenoxy, each of which is mono- or polysubstituted by identical or different substituents selected from the group consisting of halogen and straight-chain or branched alkyl having 1 to 4 carbon atoms;

heterocyclyl or heterocyclyl-methyl having in each case 3 to 7 ring members, 1 to 3 of which are in each case identical or different heteroatoms—in particular nitrogen, oxygen and/or sulphur—, or a grouping 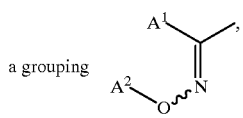

in which
$A^1$ represents alkyl having 1 to 4 carbon atoms or cycloalkyl having 1 to 6 carbon atoms and
$A^2$ represents optionally cyano-, alkoxy-, alkylthio-, alkylamino-, dialkylamino- or phenyl-substituted alkyl having 1 to 4 carbon atoms, alkenyl or alkinyl having in each case 2 to 4 carbon atoms, or a grouping 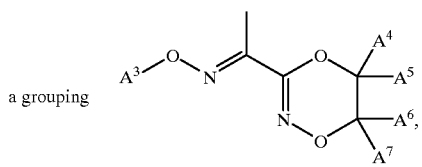

in which
$A^3$ represents alkyl having 1 to 4 carbon atoms and
$A^4$, $A^5$, $A^6$ and $A^7$ are identical or different and, independently of one another, each represents hydrogen, alkyl or hydroxyalkyl having in each case 1 to 4 carbon atoms or halogenoalkyl having 1 to 4 carbon atoms and 1 to five identical or different halogen atoms, or
$A^4$ and $A^5$ or $A^4$ and $A^6$ or $A^6$ and $A^7$ together with the respective carbon atoms to which they are attached form a cycloaliphatic ring having five, six or seven carbon atoms.

The present application relates in particular to compounds of the formula (I) in which
$R^1$ represents hydrogen, methyl, ethyl, n- or i-propyl, methoxy or ethoxy,
$Y^1$, $Y^2$, $Y^3$, $Y^4$ and $Y^5$ are identical or different and each represents hydrogen, fluorine, chlorine, bromine, cyano, methyl, ethyl, methoxy, trifluoromethyl or difluoromethoxy, and either
$Y^2$ or $Y^3$ represents —G—Z, in which
G represents one of the groupings below
—Q—CQ—, —CQ—Q—, —CQ—Q—$CH_2$—, —$CH_2$—Q—CQ—, —Q—CQ—$CH_2$—, —Q—CQ—Q—$CH_2$—, —N=N—, —S(O)$_n$—, —$CH_2$—S(O)$_n$—, —CQ—, —S(O)$_n$—$CH_2$—, —C($R^3$)=N—O—, —C($R^3$)=N—O—$CH_2$—, —N($R^4$)—, —CQ—N($R^4$)—, —N($R^4$)—CQ—, —Q—CQ—N($R^4$)—, —N=C($R^3$)—Q—$CH_2$—, —$CH_2$—O—N=C($R^3$)—, —C($CH_3$)—O—N=C($R^3$)—, —N($R^4$)—CQ—Q—, —CQ—N($R^4$)—CQ—Q—, —N($R^4$)—CQ—Q—$CH_2$—, —Q—C($R^3$)=N—O—$CH_2$—, —N($R^4$)—C($R^3$)=N—O—$CH_2$—, —O—$CH_2$—C($R^3$)=N—O—$CH_2$—, —N=N—C($R^3$)=N—O—$CH_2$—, —C(=N—O—$R^5$)—C($R^3$)=N—O—$CH_2$—, —C(=N—O—$R^5$)—C($R^3$)—O—N=CH—, —C(=N—O—$R^5$)—C($R^3$)—O—N=C($CH_3$)—, —T—$Ar^1$— or —T—$Ar^1$—Q—, where
n represents the numbers 0, 1 or 2,
Q represents oxygen or sulphur,
$R^3$ represents hydrogen, cyano, methyl, ethyl or cyclopropyl and
$R^4$ represents hydrogen, methyl, ethyl or cyclopropyl, R[5] represents hydrogen or methyl, Ar[1] represents phenylene or pyridinediyl, each of which is optionally mono- to trisubstituted by identical or different substituents, represents in each case optionally mono- substituted pyrimidinediyl, pyridazinediyl, pyrazinedlyl, 1,2,3-triazinediyl, 1,2,4-triazinediyl or 1,3,5-triazinediyl or represents 1,2,4-thiadiazolediyl, 1,3,4-thiadiazolediyl, 1,2,4-oxadiazolediyl, 1,3,4-oxadiazolediyl, where the possible substituents are preferably selected from the list below:
fluorine, chlorine, bromine, cyano, methyl, ethyl, n- or i- propyl, cyclopropyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl and
T represents a single bond, represents oxygen, sulphur, —CH$_2$—O—, CH$_2$—S—, methylene, ethylene or propylene, Z represents ethyl, n- or i-propyl, n-, i-, s- or t-butyl or methyl which is optionally mono- to trisubstituted by identical or different substituents selected from the group consisting of fluorine, chlorine, cyano and methoxy;
represents in each case optionally fluorine- or chlorine-substituted vinyl, allyl or propargyl;
represents cyclopropyl, cyclobutyl, cyclopentyl or cyclohexyl, each of which is optionally mono- to trisubstituted by identical or different substituents selected from the group consisting of fluorine, chlorine, cyano, methoxy, phenyl, methyl or ethyl; or Z represents phenyl, 1,2,4-thiadiazolyl, 1,3,4-thiadiazolyl, 1,2,4-oxadiazolyl, 1,3,4-oxadiazolyl, pyridinyl, pyrimidyl, pyridazinyl, pyrazinyl, 1,2,3-triazinyl, 1,2,4-triazinyl or 1,3,5-triazinyl, each of which is optionally mono- to trisubstituted by identical or different substituents, where the possible substituents are preferably selected from the list below:
fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl,
in each case doubly attached methylenedioxy, ethylenedioxy, each of which is optionally mono- to tetrasubstituted by identical or different substituents selected from the group consisting of fluorine, chlorine, methyl, trifluoromethyl and ethyl,
phenyl, 4-chlorophenyl, 4-methylphenyl, phenoxy, 4-chlorophenoxy, 4-methylphenoxy, cyclopropyl, cyclobutyl, cyclopentyl or cyclohexyl, or a grouping 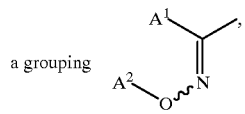

in which
A[1] represents methyl, ethyl, n- or i-propyl, n-, i-, s- or t-butyl, cyclopropyl or cyclobutyl,
A[2] represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methyl aminomethyl, methyl aminoethyl or benzyl, or a grouping 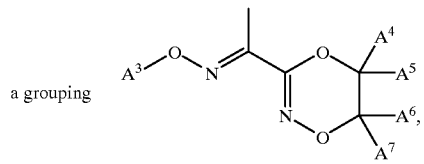

in which
A[3] represents methyl or ethyl and
A[4], A[5], A[6] and A[7] are identical or different and independently of one another each represents hydrogen, methyl, ethyl, n- or i-propyl, n-, i-, s- or t-butyl, hydroxymethyl, trifluoromethyl or trifluoroethyl, or
A[4] and A[5] or A[4] and A[6] or A[6] and A[7] together with the respective carbon atoms to which they are attached form a cycloaliphatic ring having five, six or seven carbon atoms.

A very particularly preferred groups of compounds according to the invention are those compounds of the formula (I), in which
R[1] represents hydrogen, methyl or methoxy,
Y[1], Y[2], Y[3], Y[4] and Y[5] are identical or different and each represents hydrogen, fluorine, chlorine, bromine, cyano, methyl, ethyl, methoxy, trifluoromethyl or difluoromethoxy, and either
Y[2] or Y[3] represents —G—Z, in which
G represents —C(R[3])=N—O—CH$_2$—, in which
R[3] represents methyl or cyclopropyl, and
Z represents phenyl, pyridyl or pyrimidyl, each of which is optionally mono- to trisubstituted by identical or different substituents, where the possible substituents are preferably selected from the list below:
fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, methoximinomethyl, ethoximinomethyl, methoximinoethyl, ethoximinoethyl, in each case doubly attached methylenedioxy or ethylenedioxy, each of which is optionally mono- to tetrasubstituted by identical or different substituents selected from the group consisting of fluorine, chlorine, methyl, trifluoromethyl and ethyl, and also phenyl and phenoxy.

Likewise, particularly preferred groups of compounds according to the invention are those compounds of the formula (I): in which $R^1$ represents hydrogen, methyl or methoxy.

$Y^1$, $Y^2$, $Y^3$, $Y^4$ and $Y^5$ are identical or different and each represents hydrogen, fluorine, chlorine, bromine, cyano, methyl, ethyl, methoxy, trifluoromethyl or difluoromethoxy.

$Y^2$ or $Y^3$ represents —G—Z, in which

G represents —T—$Ar^1$— or —T—$Ar^1$—O—, in which
$Ar^1$ represents 1,2,4-thiadiazolediyl, 1,3,4-thiadiazolediyl, 1,2,4-oxadiazolediyl, 1,3,4-oxadiazolediyl or represents pyridinediyl, pyrimidinediyl or 1,3,5-triazinediyl, each of which is optionally mono- or disubstituted by identical or different substituents selected from the group consisting of fluorine, chlorine, cyano, methyl, cyclopropyl, methoxy, methylthio, trifluoromethyl, difluoromethoxy, trifluoromethoxy, difluorochloromethoxy, T represents a single bond, represents oxygen, sulphur, —CH₂—O—, CH₂—S—, methylene, ethylene or propylene.

Z represents methyl, ethyl, n- or i-propyl, n-, i-, s- or t-butyl, which is optionally mono- to trisubstituted by identical or different substituents selected from the group consisting of fluorine, chlorine, cyano and methoxy;
represents in each case optionally fluorine- or chlorine-substituted vinyl, allyl or propargyl;
represents cyclopropyl, cyclobutyl, cyclopentyl or cyclohexyl, each of which is optionally mono- to trisubstituted by identical or different substituents selected from the group consisting of fluorine, chlorine, cyano, methoxy, phenyl, methyl and ethyl; or Z represents phenyl, pyridyl, pyrimidyl or thienyl, each of which is optionally mono- to trisubstituted by identical or different substituents, where the possible substituents are preferably selected from the list below:
fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl,
in each case doubly attached methylenedioxy, ethylenedioxy, each of which is optionally mono- to tetrasubstituted by identical or different substituents selected from the group consisting of fluorine, chlorine, methyl, trifluoromethyl and ethyl cyclopropyl, cyclobutyl, cyclopentyl, cyclohexyl, phenyl, phenoxy, or a grouping 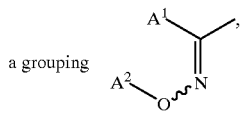

in which $A^1$ represents methyl, ethyl, n- or i-propyl, n-, i-, s- or t-butyl, cyclopropyl or cyclobutyl, $A^2$ represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl, or a grouping 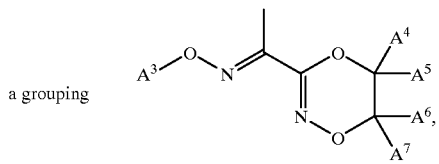

in which $A^3$ represents methyl or ethyl and $A^4$, $A^5$, $A^6$ and $A^7$ are identical or different and independently of one another each represents hydrogen, methyl, ethyl, n- or i-propyl, n-, i-, s- or t-butyl, hydroxymethyl, trifluoromethyl or trifluoroethyl, or $A^4$ and $A^5$ or $A^4$ and $A^6$ or $A^6$ and $A^7$ together with the respective carbon atoms to which they are attached form a cycloaliphatic ring having five, six or seven carbon atoms.

The abovementioned general or preferred radical definitions apply both to the end products of the formula (I) and correspondingly to the starting materials or intermediates required in each case for the preparation.

The radical definitions given in the respective combinations or preferred combinations of radicals individually for this radical are, independently of the respective given combination, replaced by any corresponding radical definition from other preferred ranges.

The compounds according to the invention are listed by way of example and by way of preference in Tables 1 to 4:

TABLE 1
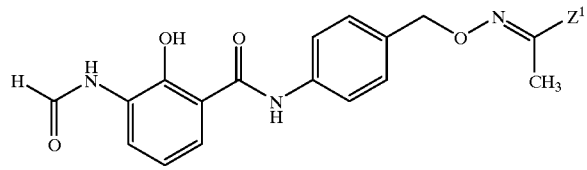
(I-a)
where Z¹ represents the following substituents:

TABLE 2
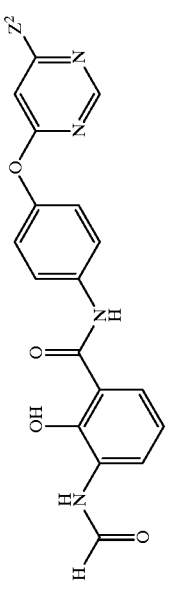
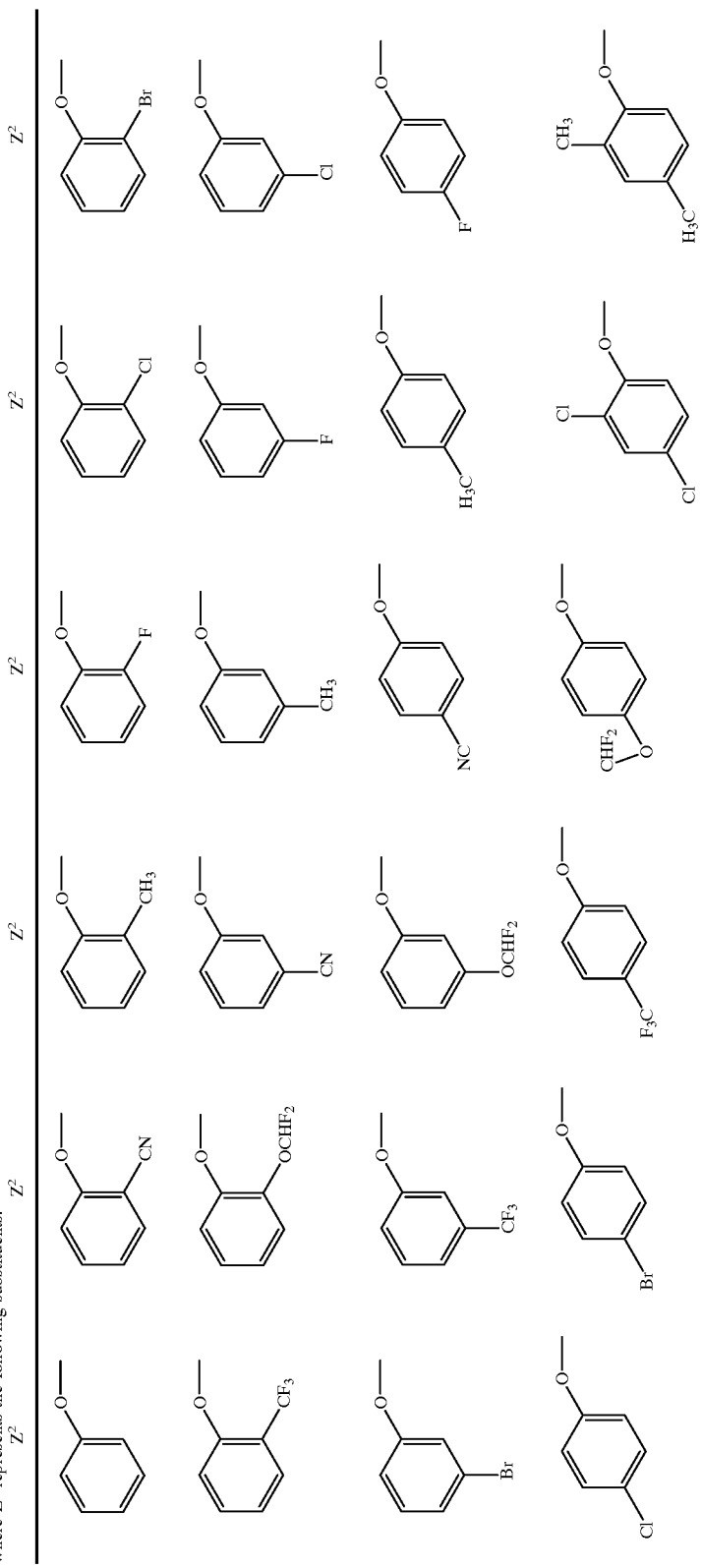
where $Z^2$ represents the following substituents:

TABLE 2-continued
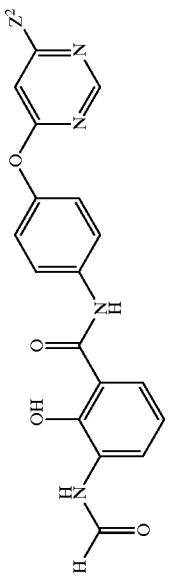
(I-b)
where $Z^2$ represents the following substituents:

TABLE 2-continued
(I-b)
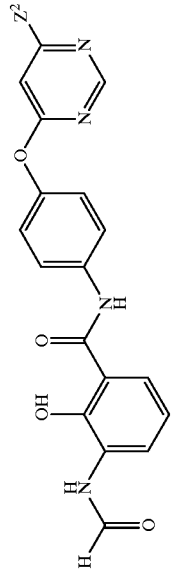
where $Z^2$ represents the following substituents:
| $Z^2$ | $Z^2$ | $Z^2$ | $Z^2$ | $Z^2$ | $Z^2$ |

TABLE 2-continued (I-b)

where $Z^2$ represents the following substituents:

TABLE 3

(I-c)

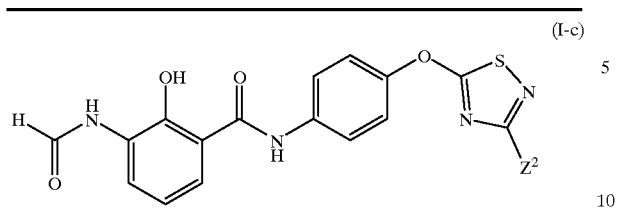

where $Z^2$ represents the substituents mentioned in Table 2.

TABLE 4

(I-d)

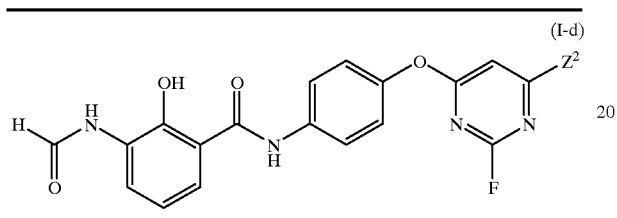

where $Z^2$ represents the substituents mentioned in Table 2.

The formula (II) provides a general definition of the aminosalicylamides required as starting materials for carrying out the process a) according to the invention. In this formula (II), $Y^1$, $Y^2$, $Y^3$, $Y^4$ and $Y^5$ each preferably or in particular have those meanings which have already been mentioned in connection with the description of the compounds of the formula (I) according to the invention as being preferred or as being particularly preferred for $Y^1$, $Y^2$, $Y^3$, $Y^4$ and $Y^5$.

The starting materials of the formula (II) are novel and also form part of the subject matter of the present application.

The aminosalicylamides of the formula (II) are obtained when (process d) nitrosalicylamides of the general formula (IV)

(IV)

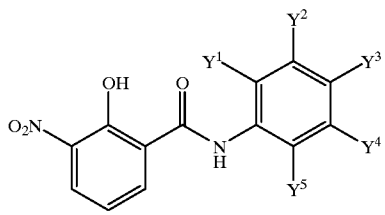

in which $Y^1$, $Y^2$, $Y^3$, $Y^4$ and $Y^5$ are each as defined above are reacted with a reducing agent, such as, for example, hydrogen, iron, zinc, tin-II chloride, sodium hydrogen sulphide or ammonium hydrogen sulphide, if appropriate in the presence of a diluent and if appropriate in the presence of a catalyst, or when (process e) O-benzyl-nitrosalicylamides of the general formula (V)

(V)

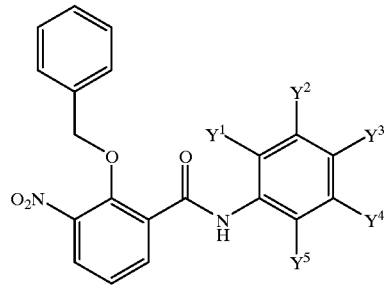

in which $Y^1$, $Y^2$, $Y^3$, $Y^4$ and $Y^5$ are each as defined above are reacted with hydrogen, if appropriate in the presence of a diluent, and if appropriate in the presence of a catalyst.

The formula (IV) provides a general definition of the nitrosalicylamides required as starting materials for carrying out the process d) according to the invention. In this formula (IV), $Y^1$, $Y^2$, $Y^3$, $Y^4$ and $Y^5$ each preferably or in particular have those meanings which have already been mentioned in connection with the description of the compounds of the formula (I) according to the invention as being preferred or as being particularly preferred for $Y^1$, $Y^2$, $Y^3$, $Y^4$ and $Y^5$.

The nitrosalicylamides of the formula (IV) are novel and also form part of the subject matter of the present application.

They are obtained when (process f) 2-hydroxy-3-nitrobenzoic acid or 2-hydroxy-3-nitrobenzoyl chloride is reacted with an amine of the formula (VII)

(VII)

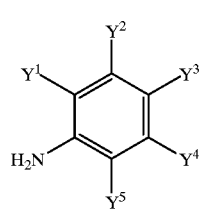

in which $Y^1$, $Y^2$, $Y^3$, $Y^4$ and $Y^5$ are each as defined above, if appropriate in the presence of a diluent, if appropriate in the presence of a condensing agent and if appropriate in the presence of an acid acceptor.

Furthermore, it has been found that the novel nitrosalicylamides of the formula (IV) are suitable for controlling pests on plants and industrial materials, preferably fungi, insects and bacteria.

The 2-hydroxy-3-nitrobenzoic acid or 2-hydroxy-3-nitrobenzoyl chloride required as starting materials for carrying out the process f) according to the invention are known (compare, for example, J.Chem.Soc., 1953 2049, 2050 or U.S. Pat. No. 03527865).

The formula (VII) provides a general definition of the amines furthermore required as starting materials for carrying out the process f) according to the invention. In this formula (VII), $Y^1$, $Y^2$, $Y^3$, $Y^4$ and $Y^5$ each preferably or in particular has those meanings which have already been mentioned in connection with the description of the compounds of the formula (I) according to the invention as being preferred or as being particularly preferred for $Y^1$, $Y^2$, $Y^3$, $Y^4$ and $Y^5$.

Some of the amines of the formula (VII) are known, and they can be prepared by known processes (compare, for example, WO-A 9601825, EP-A 192180).

Novel, and also part of the subject matter of the present application, are amines of the formula

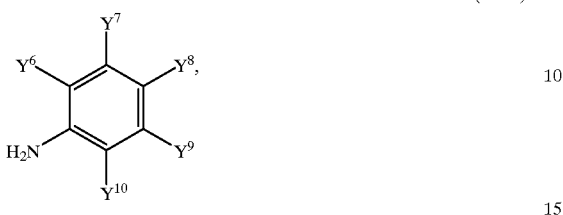

(VII-a)

in which
$Y^6$, $Y^7$, $Y^8$, $Y^9$ and $Y^{10}$ are identical or different and each represents hydrogen, halogen, cyano, alkyl, halogenoalkyl, alkoxy or halogenoalkoxy, and either $Y^7$ or $Y^8$ represents a grouping

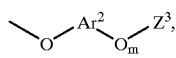

in which
m represents 0 or 1,
$Ar^2$ represents 1,2,4-oxadiazole-3,5-diyl, 1,2,4-thiadiazole-3,5-diyl or represents pyrimidin-4,6-diyl which is optionally substituted in the 5 position by halogen and
$Z^3$ represents optionally substituted aryl.

Preference is given to amines of the formula (VII-a) in which
$Y^6$, $Y^7$, $Y^8$, $Y^9$ and $Y^{10}$ are identical or different and each represents hydrogen, halogen, cyano, alkyl or alkoxy having in each case 1 to 4 carbon atoms, halogenoalkyl, or halogenoalkoxy having in each case 1 to 4 carbon atoms and 1 to 5 identical or different halogen atoms, and either
$Y^7$ or $Y^8$ represents a grouping

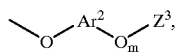

in which
m represents 0 or 1,
$Ar^2$ represents 1,2,4-oxadiazole-3,5-diyl, 1,2,4-thiadiazole-3,5-diyl or represents pyrimidine-4,6-diyl which is optionally substituted in the 5 position by fluorine or chlorine and
$Z^3$ represents phenyl or naphthyl, each of which is optionally mono- or polysubstituted by identical or different substituents, where the possible substituents are preferably selected from the list below:
halogen, cyano, amino, hydroxyl, formyl, carboxyl, carbamoyl, thiocarbamoyl;
in each case straight-chain or branched alkyl, alkoxy, alkylthio, alkylsulphinyl or alkylsulphonyl having in each case 1 to 6 carbon atoms;
in each case straight-chain or branched alkenyl or alkenyloxy having in each case 2 to 6 carbon atoms;
in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;
in each case straight-chain or branched halogenoalkenyl or halogenoalkenyloxy having in each case 2 to 6 carbon atoms and 1 to 11 identical or different halogen atoms;
in each case straight-chain or branched alkylamino, dialkylamino, alkylcarbonyl, alkylcarbonyloxy, alkoxycarbonyl or alkylsulphonyloxy, having in each case 1 to 6 carbon atoms in the individual alkyl moieties;
in each case doubly attached alkylene or dioxyalkylene having in each case 1 to 6 carbon atoms and being in each case optionally mono- or polysubstituted by identical or different substituents selected from the group consisting of halogen, straight-chain or branched alkyl having 1 to 4 carbon atoms and straight-chain or branched halogenoalkyl having 1 to 4 carbon atoms and 1 to 9 identical or different halogen atoms;
cycloalkyl having 3 to 6 carbon atoms;
phenyl or phenoxy, each of which is optionally mono- or polysubstituted by identical or different substituents selected from the group consisting of halogen and straight-chain or branched alkyl having 1 to 4 carbon atoms;
heterocyclyl or heterocyclyl-methyl having in each case 3 to 7 ring members, 1 to 3 of which are in each case identical or different heteroatoms—in particular nitrogen, oxygen and/or sulphur-, or a grouping 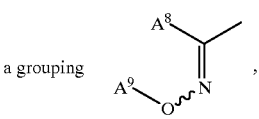

in which
$A^8$ represents alkyl having 1 to 4 carbon atoms or cycloalkyl having 1 to 6 carbon atoms and
$A^9$ represents optionally cyano-, alkoxy-, alkylthio-, alkylamino-, dialkylamino- or phenyl-substituted alkyl having 1 to 4 carbon atoms, alkenyl or alkinyl having in each case 2 to 4 carbon atoms, or a grouping 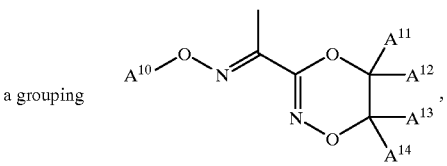

in which
$A^{10}$ represents alkyl having 1 to 4 carbon atoms and
$A^{11}$, $A^{12}$, $A^{13}$ and $A^{14}$ are identical or different and, independently of one another, each represents hydrogen, alkyl or hydroxyalkyl having in each case 1 to 4 carbon atoms or halogenoalkyl having 1 to 4 carbon atoms and 1 to five identical or different halogen atoms, or $A^{11}$ and $A^{12}$ or $A^{11}$ and $A^{13}$ or $A^{13}$ and $A^{14}$ together with the respective carbon atoms to which they are attached form a cycloaliphatic ring having five, six or seven carbon atoms.

Particular preference is given to amines of the formula (VII-a) in which $Y^6$, $Y^7$, $Y^8$, $Y^9$ and $Y^{10}$ are identical or different and each represents hydrogen, fluorine, chlorine, bromine, cyano, methyl, ethyl, methoxy, trifluoromethyl or difluoromethoxy, and either $Y^7$ or $Y^8$ represents a grouping

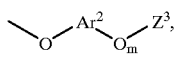

in which m represents 0 or 1, $Ar^2$ represents 1,2,4-oxadiazole-3,5-diyl, 1,2,4-thiadiazole-3,5-diyl or represents pyrimidine-4,6-diyl which is optionally substituted in the 5 position by fluorine or chlorine and $Z^3$ represents phenyl which is in each case optionally mono- to trisubstituted by identical or different substituents, where the possible substituents are preferably selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, in each case doubly attached methylenedioxy, ethylenedioxy, each of which is optionally mono- to tetrasubstituted by identical or different substituents selected from the group consisting of fluorine, chlorine, methyl, trifluoromethyl or ethyl phenyl, 4-chlorophenyl, 4-methylphenyl, phenoxy, 4-chlorophenoxy, 4-methylphenoxy, cyclopropyl, cyclobutyl, cyclopentyl or cyclohexyl, or a grouping 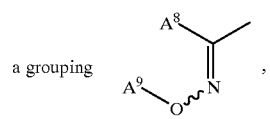

in which $A^8$ represents methyl, ethyl, n- or i-propyl, n-, i-, s- or t-butyl, cyclopropyl or cyclobutyl, $A^9$ represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl, or a grouping 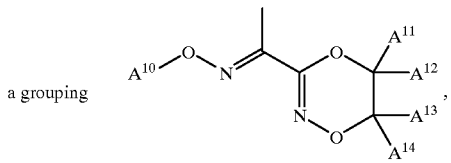

in which $A^{10}$ represents methyl or ethyl and $A^{11}$, $A^{12}$, $A^{13}$ and $A^{14}$ are identical or different and, independently of one another, each represents hydrogen, methyl, ethyl, n- or i-propyl, n-, i-, s- or t-butyl, hydroxymethyl, trifluoromethyl or trifluoroethyl, or $A^{11}$ and $A^{12}$ or $A^{11}$ and $A^{13}$ or $A^{13}$ and $A^{14}$ together with the respective carbon atoms to which they are attached form a cycloaliphatic ring having five, six or seven carbon atoms.

The amines of the formula (VII-a) are obtained (process h) when diazoles of the general formula (VIII) or halogenopyrimidines of the general formula (IX)

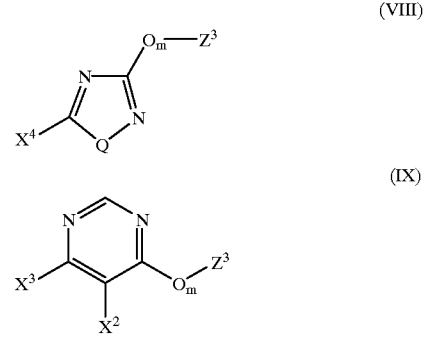

in which m represents 0 or 1, $X^2$ represents hydrogen, fluorine or chlorine, $X^3$ represents chlorine or fluorine, $X^4$ represents methylsulphonyl, chlorine or bromine and Q represents oxygen or sulphur, and $Z^3$ is as defined above are reacted with an aminophenol of the formula

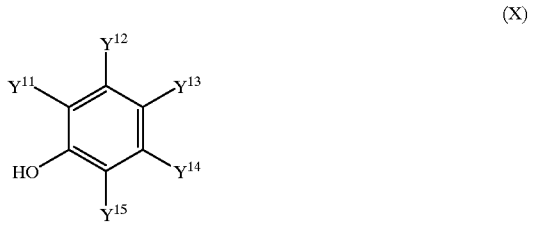

in which $Y^{11}$, $Y^{12}$, $Y^{13}$, $Y^{14}$ and $Y^{15}$ are identical or different and each represents hydrogen, halogen, cyano, alkyl, halogenoalkyl, alkoxy or halogenoalkoxy, and either $Y^{12}$ or $Y^{13}$ represents amino, if appropriate in the presence of a diluent, if appropriate in the presence of an acid acceptor and if appropriate in the presence of a catalyst, or when (process i) aminophenoxypyrimidines of the general formula (XI)

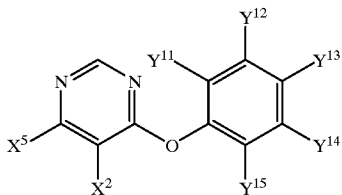

(XI)

in which
X², Y¹¹, Y¹², Y¹³, Y¹⁴ and Y¹⁵ are each as defined above and
X⁵ represents chlorine or fluorine, are reacted with a phenol of the general formula (XII),

Z³—OH (XII)

in which
Z³ is as defined above, if appropriate in the presence of a diluent, if appropriate in the presence of an acid acceptor and if appropriate in the presence of a catalyst.

The formula (VIII) provides a general definition of the diazoles required as starting materials for carrying out the process h) according to the invention. In this formula (VIII), m and Z³ each preferably or in particular have those meanings which have already been mentioned in connection with the description of the compounds of the formula (VII-a) according to the invention as being preferred or as being particularly preferred for m and Z³. X⁴ represents methylsulphonyl, chlorine or bromine.

The diazoles of the formula (VIII) are known, and they can be prepared by known methods (compare, for example, DE-A 2142913).

The formula (IX) provides a general definition of the halogenopyrimidines alternatively required as starting materials for carrying out the process h) according to the invention. In this formula (IX), m and Z³ each preferably or in particular have those meanings which have already been mentioned in connection with the description of the compounds of the formula (VII-a) according to the invention as being preferred or as being particularly preferred for m and Z³. X² represents hydrogen, fluorine or chlorine. X³ represents fluorine or chlorine.

Some of the halogenopyrimidines of the formula (IX) are known, and they can be prepared by known methods (cf. for example, Pharm.Chem.J.(Engl.Transl.), 23, 6, 1989, 500–503; RU, 23, 6, 1989, 705–707).

Novel, and also part of the subject matter of the present application, are 4-chloro-5-fluoro-6-phenoxypyrimidines of the general formula

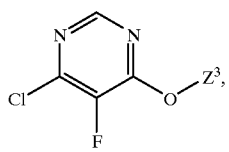

(IX-a)

in which
Z³ is as defined above, except for the compound methyl 2-[(6-chloro-5-fluoro-4-pyrimidinyl)-oxy]-α-(methoxymethylene)-benzoate.

The novel 4-chloro-5-fluoro-6-phenoxypyrimidines are obtained when (process j) phenols of the general formula (XII),

Z³—OH (XII)

in which
Z³ is as defined above are reacted with 4,6-dichloro-5-fluoropyrimidine (XIII), if appropriate in the presence of a diluent, if appropriate in the presence of an acid acceptor and if appropriate in the presence of a catalyst.

The formula (XII) provides a general definition of the phenols required as starting materials for carrying out the process j) according to the invention. In this formula (XII), Z³ preferably or in particular has the meaning which has already been mentioned in connection with the description of the compounds of the formula (VII-a) according to the invention as being preferred or as being particularly preferred for Z³.

The phenols of the formula (XII) are known chemicals for synthesis, or they can be prepared by known processes (WO 95-04728).

The 4,6-dichloro-5-fluoropyrimidine (XIII) furthermore required as starting material for carrying out the process j) according to the invention is novel and also forms part of the subject matter of the present application.

It is obtained when (process k) 5-fluoro-6-hydroxy-4(1H)-pyrimidinone (XIV) is reacted with a chlorinating agent, if appropriate in the presence of a diluent and if appropriate in the presence of a catalyst.

The 5-fluoro-6-hydroxy-4(1H)-pyrimidinone (XIV) required as starting material for carrying out the process k) according to the invention is known and can be prepared by known methods (JP 61205262; CA: 106:84632).

The formula (XI) provides a general definition of the aminophenoxypyrimidines required as starting materials for carrying out the process i) according to the invention. In this formula (XI), Y¹¹, Y¹², Y¹³, Y¹⁴ and Y¹⁵ each preferably or in particular have those meanings which have already been mentioned in connection with the description of the amines of the formula (X) as being preferred or as being particularly preferred for Y¹¹, Y¹², Y¹³, Y¹⁴ and Y¹⁵. X² and X⁵ independently of one another each represent chlorine or fluorine.

The aminophenoxypyrimidines of the formula (XI) are novel and also form part of the subject matter of the present application.

They are obtained when (process l) trihalogenopyrimidines of the formula (XV)

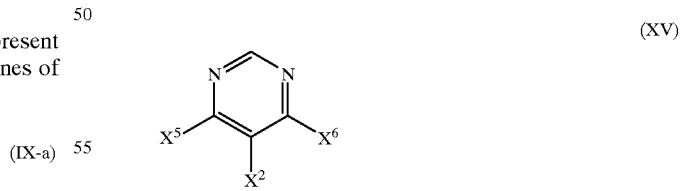

(XV)

in which
X² and X⁵ are each as defined above and
X⁶ represents fluorine or chlorine are reacted with an aminophenol of the formula (X) if appropriate in the presence of a diluent, if appropriate in the presence of an acid acceptor and if appropriate in the presence of a catalyst.

The formula (XV) provides a general definition of the trihalogenopyrimidines required as starting materials for carrying out the process l) according to the invention. In this formula (XV), $X^2$ and $X^5$ each preferably or in particular have those meanings which have already been mentioned in connection with the description of the compounds of the formula (XI) as being preferred or as being particularly preferred for $X^2$ and $X^5$. $X^6$ represents fluorine or chlorine.

Some of the trihalogenopyrimidines of the formula (XV) are known, and they can be prepared by known methods (compare, for example, Chesterfield et al., J. Chem. Soc., 1955; 3478, 3480). A special case of the compounds of the formula (XV) is the compound (XIII) according to the invention; it can be prepared by process k).

The aminophenols of the formula (X) furthermore required as starting materials for carrying out the process l) according to the invention have already been described further above in the description of the process h) according to the invention.

The phenols of the formula (XII) furthermore required as starting materials for carrying out the process i) according to the invention have already been described further above in the description of the process j) according to the invention.

The formula (V) provides a general definition of the O-benzyl-nitrosalicylamides required as starting materials for carrying out the process e) according to the invention. In this formula (V), $Y^1$, $Y^2$, $Y^3$, $Y^4$ and $Y^5$ each preferably or in particular have those meanings which have already been mentioned in connection with the description of the compounds of the formula (I) according to the invention as being preferred or as being particularly preferred for $Y^1$, $Y^2$, $Y^3$, $Y^4$ and $Y^5$.

The O-benzyl-nitrosalicylamides of the formula (V) have hitherto not been known, as novel substances, they form part of the subject matter of the present application.

The O-benzyl-nitrosalicylamides of the formula (V) are obtained when (process g) O-benzyl-nitrosalicylic acid derivatives of the formula (VI),

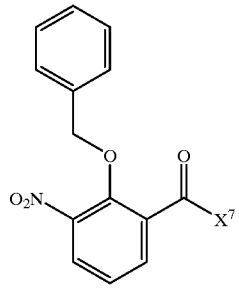

(VI)

in which
X⁷ represents halogen, hydroxyl or alkoxy, are reacted with an amine of the formula (VII), if appropriate in the presence of a diluent, if appropriate in the presence of a condensing agent and if appropriate in the presence of an acid acceptor.

The formula (VI) provides a general definition of the O-benzyl-nitrosalicylic acid derivatives required as starting materials for carrying out the process g) according to the invention. In this formula (VI), $X^7$ represents halogen, preferably chlorine; hydroxyl or alkoxy, preferably methoxy or ethoxy.

The O-benzyl-nitrosalicylic acid derivatives of the formula (VI) are known, and they can be prepared by known methods (compare, for example, J. Am. Chem. Soc. 1959, 5215–5217).

The amines of the formula (VII) furthermore required as starting materials for carrying out the process g) according to the invention have already been described further above in connection with the description of the process f) according to the invention.

The formula (III) provides a general definition for the acylating agents furthermore required as starting materials for carrying out the process a) according to the invention. In this formula (III), $R^1$ preferably or in particular has the meaning which has already been mentioned in connection with the description of the compounds of the formula (I) according to the invention as being preferred or as being particularly preferred for $R^1$. $X^1$ represents halogen, hydroxyl, alkoxy or alkylcarbonyloxy, preferably chlorine, hydroxyl, methoxy, ethoxy or acetoxy.

The acylating agents of the general formula (III) are known reagents in organic chemistry.

The nitrosalicylamides of the formula (IV) required as starting materials for carrying out the process b) according to the invention have already been described further above in connection with the description of the process d) according to the invention.

The O-benzyl-nitrosalicylamides of the formula (V) required as starting materials for carrying out the process c) according to the invention have already been described further above in connection with the description of the process e) according to the invention.

Suitable diluents for carrying out the processes a), f) and g) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decaline; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters such as methyl acetate or ethyl acetate; sulphoxides, such as dimethyl sulphoxide or sulphones, such as sulpholane.

Suitable diluents for carrying out the processes d) and e) according to the invention are all inert organic solvents. These preferably include esters such as methyl acetate or ethyl acetate; alcohols, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, water, salt solutions, such as, for example, ammonium chloride solution, acids, such as, for example, hydrochloric acid or acetic acid, and also any mixtures of the abovementioned diluents.

Suitable diluents for carrying out the processes h), i), j) and l) according to the invention are all inert organic solvents. These preferably include ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; sulphoxides, such as dimethyl sulfoxide; or sulphones, such as sulpholane.

Suitable diluents for carrying out the process k) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decaline; halogenated hydrocarbons, such as, for example, chlorobenzene, dichlorobenzene, dichloromethane, chloroform, carbon tetrachloride, dichloroethane or trichloroethane; nitriles, such as acetonitrile, propionitrile, n- or i-butyronitrile or benzonitrile.

The processes a), f) and g) according to the invention are, if appropriate, carried out in the presence of a suitable acid acceptor. Suitable acid acceptors are all customary inorganic or organic bases. These preferably include alkaline earth metal or alkali metal hydroxides, acetates, carbonates or bicarbonates, such as, for example, sodium hydroxide, potassium hydroxide, sodium acetate, potassium acetate, calcium acetate, sodium carbonate, potassium carbonate, potassium bicarbonate or sodium bicarbonate, and also tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The processes b), c), d) and e) according to the invention are, if appropriate, carried out in the presence of a catalyst. Suitable catalysts are all catalysts which are also usually employed for hydrogenations. Examples include: Raney nickel, palladium or platinum, if appropriate on a support, such as, for example, activated carbon.

The process c) according to the invention is, if appropriate, also carried out in the presence of hydrogen or, if appropriate, in the presence of a base metal. Suitable base metals are, for example: zinc, tin, iron, aluminium or magnesium.

Suitable further reaction auxiliaries for carrying out the processes a), b) and c) according to the invention are all dehydrating agents, in particular acetic anhydride.

The processes f) and g) according to the invention are, if appropriate, carried out in the presence of a condensing agent. These preferably include acyl halide formers such as, for example, phosgene, phosphorus tribromide, phosphorus trichloride, phosphorus pentachloride, phosphorus oxychloride or thionyl chloride; anhydride formers such as ethyl chloroformate, methyl chloroformate, isopropyl chloroformate, isobutyl chloroformate or methanesulphonyl chloride; carbodiimides, such as N,N'-dicyclohexylcarbodiimide (DCC) or other customary condensing agents, such as phosphorus pentoxide, polyphosphoric acid, N,N'-carbonyldiimidazole, 2-ethoxy-N-ethoxycarbonyl-1,2-dihydroquinoline (EEDQ) or triphenylphosphine/carbon tetrachloride.

The processes h), i), j) and l) according to the invention are, if appropriate, carried out in the presence of a suitable acid acceptor. Suitable acid acceptors are all customary inorganic or organic bases. These preferably include alkaline earth metal or alkali metal hydrides, hydroxides, alkoxides, carbonates or bicarbonates, such as, for example, sodium hydride, sodium amide, potassium tert-butoxide, sodium hydroxide, potassium hydroxide, sodium carbonate, potassium carbonate, potassium bicarbonate or sodium bicarbonate.

Suitable catalysts for processes h), i), j) and l) according to the invention are all copper(I) salts, such as, for example, copper(I) chloride, copper(I) bromide or copper(I) iodide, or else fluorides, such as, for example, sodium fluoride, potassium fluoride or ammonium fluoride, and also tertiary ammonium fluorides, such as tetrabutylammonium fluoride.

The process k) according to the invention is, if appropriate, carried out in the presence of a suitable catalyst. Suitable catalysts are all tertiary amines, such as, for example, trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU), and also amides, such as dimethylformamide.

Suitable halogenating agents for carrying out the process k) according to the invention are all reagents which are capable of exchanging hydroxyl groups which are attached to carbon for chlorine. Examples include: phosgene, phosphorus trichloride, phosphorus pentachloride, phosphorus oxychloride or thionyl chloride and, if appropriate, additionally hydrogen chloride or chlorine.

When carrying out the processes a), b), c), d), e), f) and g) according to the invention, the reaction temperatures can be varied within a relatively wide range. In general, the processes are carried out at temperatures from 0° C. to 180° C., preferably at temperatures from 0° C. to 130° C.

When carrying out the processes h), i), j) and l) according to the invention, the reaction temperatures can be varied within a relatively wide range. In general, the processes are carried out at temperatures from −20° C. to 200° C., preferably at temperatures from −10° C. to 150° C.

When carrying out the process k) according to the invention, the reaction temperatures can be varied within a relatively wide range. In general, the process is carried out at temperatures from 0° C. to 250° C., preferably at temperatures from 0° C. to 200° C.

For carrying out the process a) according to the invention for preparing the compounds of the formula (I), generally from 1 to 2000 mol, preferably from 1 to 800 mol, of acylating agent of the formula (III) are employed per mole. of the aminosalicylamide of the formula (II).

For carrying out the processes b) and c) according to the invention for preparing the compounds of the formula (I), generally from 100 to 2000 mol, preferably from 200 to 1000 mol, of formic acid are employed per mole of the nitrosalicylamide of the formula (IV), or of the O-benzyl-nitrosalicylamide of the formula (V).

For carrying out the process d) according to the invention for preparing the compounds of the formula (II), generally from 1 to 100 mol, preferably from 2 to 20 mol, of reducing agent are employed per mole of the nitrosalicylamide of the formula (IV).

For carrying out the process e) according to the invention for preparing the compounds of the formula (II), generally from 1 to 100 mol, preferably from 2 to 50 mol, of hydrogen are employed per mole of the O-benzyl-nitrosalicylamide of the formula (V).

For carrying out the process f) according to the invention for preparing the compounds of the formula (IV), generally from 0.5 to 10 mol, preferably from 0.8 to 5 mol, of 2-hydroxy-3-nitrobenzoic acid or 2-hydroxy-3-nitrobenzoyl chloride are employed per mole of amine of the formula (VII).

For carrying out the process g) according to the invention for preparing the compounds of the formula (V), generally from 0.5 to 10 mol, preferably from 0.8 to 5 mol, of O-benzyl-nitrosalicylic acid derivatives of the formula (VI) are employed per mole of the amine of the formula (VII).

For carrying out the process h) according to the invention for preparing the compounds of the formula (VII-a), generally from 0.5 to 5 mol, preferably from 0.8 to 2 mol, of halogenopyrimidine of the formula (IX) or diazole of the formula (VIII) are employed per mole of the aminophenol of the formula (X).

For carrying out the process i) according to the invention for preparing the compounds of the formula (VII-a), generally from 0.5 to 5 mol, preferably from 0.8 to 2 mol, of aminophenoxypyrimidine (XI) are employed per mole of the phenol of the formula (XII).

For carrying out the process j) according to the invention for preparing the compounds of the formula (IX-a), generally from 0.5 to 5 mol, preferably from 0.8 to 2 mol, of 4,6-dichloro-5-fluoropyrimidine (XIII) are employed per mole of the phenol of the formula (XII).

For carrying out the process k) according to the invention for preparing 4,6-dichloro-5-fluoropyrimidine (XIII), generally from 0.05 to 20 mol, preferably from 0.1 to 10 mol, of halogenating agent are employed per mole of 5-fluoro-6-hydroxy-4(1H)-pyrimidinone (XIV).

For carrying out the process l) according to the invention for preparing the compounds of the formula (XI), generally from 0.5 to 5 mol, preferably from 0.8 to 2 mol, of trihalogenopyrimidine (XV) are employed per mole of the aminophenol of the formula (X).

The processes a) to l) according to the invention are generally carried out under atmospheric pressure. However, it is also possible to operate under elevated or reduced pressure—in general between 0.1 bar and 10 bar.

The compounds according to the invention have potent microbicidal activity and can be employed for controlling undesirable microorganisms, such as fungi and bacteria, in crop protection and in the protection of materials.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris* pv. *oryzae;*
Pseudomonas species, such as, for example, *Pseudomonas syringae* pv. *lachrymans;*
Erwinia species, such as, for example, *Erwinia amylovora;*
Pythium species, such as, for example, *Pythium ultimum;*
Phytophthora species, such as, for example, *Phytophthora infestans;*
Pseudoperonospora species, such as, for example, *Pseudoperonospora humuli* or *Pseudoperonospora cubensis;*
Plasmopara species, such as, for example, *Plasmopara viticola;*
Bremia species, such as, for example, *Bremia lactucae;*
Peronospora species, such as, for example, *Peronospora pisi* or *P. brassicae;*
Erysiphe species, such as, for example, *Erysiphe graminis;*
Sphaerotheca species, such as, for example, *Sphaerotheca fuliginea;*
Podosphaera species, such as, for example, *Podosphaera leucotricha;*
Venturia species, such as, for example, *Venturia inaequalis;*
Pyrenophora species, such as, for example, *Pyrenophora teres* or *P. graminea* (conidia form: Drechslera, syn: Helminthosporium);
Cochliobolus species, such as, for example, *Cochliobolus sativus* (conidia form: Drechslera, syn: Helminthosporium);
Uromyces species, such as, for example, *Uromyces appendiculatus;*
Puccinia species, such as, for example, *Puccinia recondita;*
Sclerotinia species, such as, for example, *Sclerotinia sclerotiorum*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae;*
Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling diseases in fruit and vegetable growing and viticulture, such as, for example, against Venturia Phytophthora species. They are also very successfully used for controlling cereal diseases, such as, for example, Pseudocercosporella species, or for controlling rice diseases, such as, for example, Pyricularia species.

The active compounds according to the invention are also suitable for increasing the harvest yield. Moreover, they show reduced toxicity and are well tolerated by plants.

Depending on their particular physical and/or chemical properties, the active compounds can be converted into the customary formulations, such as solutions, emulsions, suspensions, powders, foams, pastes, granules, aerosols and micro-encapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam-formers. If the extender used is water, it is also possible to employ, for example, organic solvents as auxiliary solvents. Essentially, the following are suitable for use as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other suitable additives are mineral and vegetable oils.

It is possible to use colourants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

Depending on their particular physical and/or chemical properties, the active compounds can be converted into the customary formulations, such as solutions, emulsions, suspensions, powders, foams, pastes, granules, aerosols and micro-encapsulations in polymeric substances and in coating compositions for seeds, and ULV cool and warm fogging formulations.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of co-components in mixtures are the following compounds:

Fungicides aldimorph, ampropylfos, ampropylfos potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, ediphenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfosufen (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene(PCNB), sulphur and sulphur preparations, tebuconazole, tecloftalam, tecnazene, tetcyclasis, tetraconazole, thiabendazole, thicyofen, thifluzamide, thiophanate-methyl, thiram, tioxymid, toiclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-b-propyl-1H-1,2,4-triazole-1-ethanol,

α-(2,4-dichlorophenyl)-β-methoxy-a-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-a-(methoxyimino)-N-methyl-2-phenoxy-phenylacetamide, isopropyl {2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone-O-(phenylmethyl)-oxime, 1-(2-methyl-1-naphthalenyl)-1H-pyrrol-2,5-dione, 1-(3,5-dichlorophenyl)-3-(2-propenyl)-2,5-pyrrolidindione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinole,
2',6'-dibromo-2-methyl-4'-trifluoromethoxy-4'-trifluoromethyl-1,3-thiazole-5-carboxanilide,
2,2-dichloro-N-[1-(4-chlorophenyl)-ethyl]-1-ethyl-3-methyl-cyclopropanecarboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)sulphonyl]-5-(trichloromethyl)-1,3,4-thiadiazole,
2-[[6-deoxy-4-O-(4-O-methyl-β-D-glycopyranosyl)-a-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrol-2,5-dione,
3,5-dichloro-N-[cyano[(1-methyl-2-propinyl)-oxy]-methyl]-benzamide,
3-(1,1-dimethylpropyl-1-oxo-1H-indene-2-carbonitrile,
3-[2-(4-chlorophenyl)-5-ethoxy-3-1soxazolidinyl]-pyridine,
4-chloro-2-cyano-N,N-dimethyl-5-(4-methylphenyl)-1H-imidazole-1-sulfonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methaneamine,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethylmorpholinehydrochloride,
ethyl[(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitrobenzenesulfonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis-(2-propinyloxy)-phenyl]-N'-methoxy-methaneimidamide,
N-formyl-N-hydroxy-DL-alanine sodium salt,
O,O-diethyl[2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one,
Bactericides
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.
Insecticides/Acaricides/Nematicides
abamectin, acephate, acrinathrin, alanycarb, aldicarb, alphamethrin, amitraz, avermectin, AZ 60541, azadirachtin, azinphos A, azinphos M, azocyclotin,
Bacillus thuringiensis, 4-bromo-2-(4-chlorophenyl)-1-(ethoxymethyl)-5-(trifluoromethyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, N-[(6-chloro-3-pyridinyl)-methyl]-N'-cyano-N-methyl-ethanimidamide, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine,
deltamethrin, demeton M, demeton S, demeton S-methyl, diafenthiuron, diazinon, dichlofenthion, dichlorvos, dicliphos, dicrotophos, diethion, diflubenzuron, dimethoate, dimethylvinphos, dioxathion, disulfoton,
edifenphos, emamectin, esfenvalerate, ethiofencarb, ethion, ethofenprox, ethoprophos, etrimphos,
fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb,
HCH, heptenophos, hexaflumuron, hexythiazox,
imidacloprid, iprobenfos, isazophos, isofenphos, isoprocarb, isoxathion, ivermectin,
lambda-cyhalothrin, lufenuron,
malathion, mecarbam, mervinphos, mesulfenphos, metaldehyde, methacrifos, methamidophos, methidathion, methiocarb, methomyl, metolcarb, milbemectin, monocrotophos, moxidectin,
naled, NC 184, nitenpyram,
omethoate, oxamyl, oxydemethon M, oxydeprofos,
parathion A, parathion M, permethrin, phenthoate, phorate, phosalone, phosmet, phosphamidon, phoxim, pirimicarb, pirimiphos M, pirimiphos A, profenophos, promecarb, propaphos, propoxur, prothiofos, prothoate, pymetrozin, pyrachlophos, pyridaphenthion, pyresmethrin, pyrethrum, pyridaben, pyrimidifen, pyriproxifen,
quinalphos,
salithion, sebufos, silafluofen, sulfotep, suiprofos,
tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

It is also possible to admix other known active compounds, such as herbicides, fertilizers and growth-regulating substances.

The active compounds can be used as such or in the form of their commercial formulations or the use forms prepared therefrom, such as ready-to-use solutions, suspensions, wettable powders, pastes, soluble powders, dusts and granules. They are used in the customary manner, for example by pouring, spraying, atomizing, spreading, dusting, foaming, brushing-on and the like. It is further possible to apply the by the ultra-low volume method or to inject the preparation of active compound, or the active compound itself, into the soil. The seed of the plants can also be treated.

When using the active compounds according to the invention as fungicides, the application rates can be varied within a relatively wide range, depending on the type of application. In the treatment of parts of plants, the active compound application rates are generally between 0.1 and 10,000 g/ha, preferably between 10 and 1000 g/ha. In the treatment of seeds, the active compound application rates are generally between 0.001 and 50 g per kilogram of seed, preferably between 0.01 and 10 g per kilogram of seed. In the treatment of soil, the active compound application rates are generally between 0.1 and 10,000 g/ha, preferably between 1 and 5000 g/ha.

Preparation Examples

EXAMPLE (1)

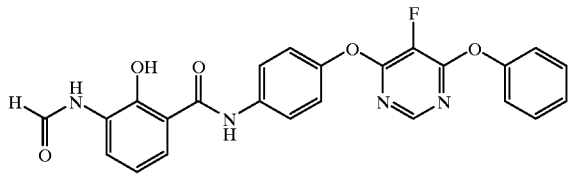

Process c)

1.67 g (3.02 mmol) of 2-benzyloxy-N-[4-(5-fluoro-6-phenoxy-pyrimidin-4-yloxy)-phenyl]-3-nitro-benzamide in 20 ml of formic acid are stirred with 0.4 g of Raney nickel at 40° C. for 24 hours. The mixture is poured into water and extracted repeatedly with ethyl acetate. The combined organic phases are dried over sodium sulphate and concentrated under reduced pressure. The residue is chromatographed over silica gel using cyclohexane/ethyl acetate (1:1). This gives 0.4 g (35% of theory) of N-[4-(5-fluoro-6-phenoxy-pyrimidin-4-yloxy)-phenyl]-3-formyl-amino-2-hydroxy-benzamide as a colourless oil.

HPLC: log P=3.31

EXAMPLE (1)

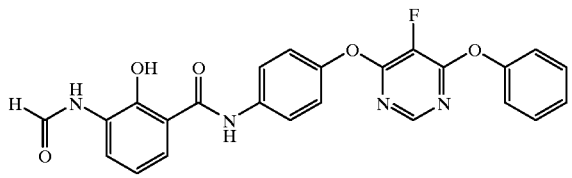

Process b)

0.5 g (1.08 mmol) of N-[4-(5-fluoro-6-phenoxy-pyrimidin-4-yloxy)-phenyl]-2-hydroxy-3-nitrobenzamide in 10 ml of formic acid are stirred with 0.5 g of Raney nickel at 40° C. for 24 hours. The mixture is poured into water and extracted repeatedly with ethyl acetate. The combined organic phases are dried over sodium sulphate and concentrated under reduced pressure. The residue is chromatographed over silica gel using cyclohexane/ethyl acetate (1:1). This gives 0.4 g (81% of theory) of N-[4-(5-fluoro-6-phenoxy-pyrimidin-4-yloxy)-phenyl]-3-formyl-amino-2-hydroxy-benzamide as a colourless oil.

HPLC: log P=3.31

Preparation of Compounds of the Formula (IV)

EXAMPLE (IV-1)

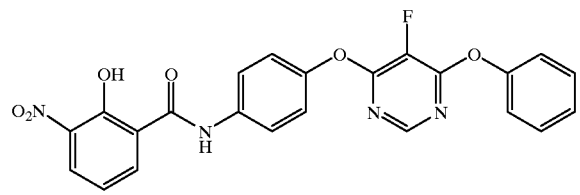

Process f)

A mixture of 1.7 g (9 mmol) of 3-nitrosalicylic acid and 2.7 g (9 mmol) of 4-(5-fluoro-6-phenoxy-pyrimidin-4-yloxy)-phenylamine in 20 ml of toluene is heated with stirring to 50° C. 0.5 g of phosphorus trichloride is added, and the mixture is heated at the boil under reflux for a further 4 hours. After cooling, the mixture is concentrated and the residue is extracted with dichloromethane. The organic phase is washed repeatedly with water and dried over sodium sulphate. The solvent is distilled off, giving 1.7 g (41% of theory) of N-[4-(5-fluoro-6-phenoxy-pyrimidin-4-yloxy)-phenyl]-2-hydroxy-3-nitrobenzamide.

Mass spectrum: m/e=462 (M+)

Preparation of Compounds of the Formula (V)

EXAMPLE (V-1)

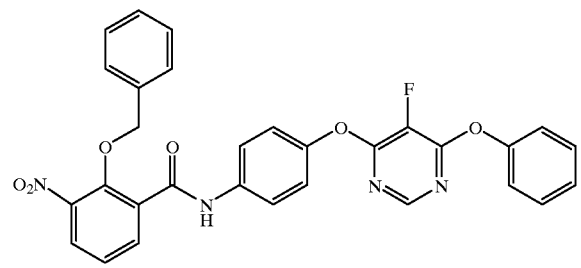

Process g)

At 0° C., a solution of 2.4 g (0.011 mol) of triethylamine and 5.3 g (18 mmol) of 4-(5-fluoro-6-phenoxy-pyrimidin-4-yloxy)-phenylamine in 30 ml of dichloromethane is added dropwise to a solution of 4.3 g (18 mmol) of 2-benzyloxy-3-nitro-benzoyl chloride in 20 ml of dichloromethane, and the mixture is stirred without further cooling for another 2 hours. The mixture is filtered and the filtrate is washed with water, dried over sodium sulphate and concentrated under reduced pressure. The residue is chromatographed over silica gel using cyclohexane/ethyl acetate (2:1). This gives 2.8 g (30% of theory) of 2-benzyloxy-N-[4-(5-fluoro-6-phenoxy-pyrimidin-4-yloxy)-phenyl]-3-nitro-benzamide as an oil.

HPLC: log P=4.56

Preparation of Compounds of the Formula (IX-a)

EXAMPLE (IX-a-1)

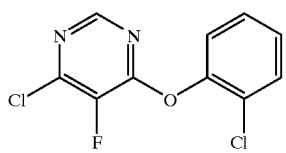

Process j)

To a mixture of 5 g (0.0295 mol) of 4,6-dichloro-5-fluoropyrimidine and 5 g (0.036 mol) of potassium carbonate in 25 ml of acetonitrile is heated to 50° C. At this temperature, a solution of 3.8 g (0.03 mol) of 2-chlorophenol in 25 ml of acetonitrile is added dropwise over a period of 6 hours, and the mixture is stirred at this temperature for a further 6 hours. After cooling, the solvent is distilled off under reduced pressure and the residue is taken up in water and extracted repeatedly with in each case 40 ml of dichloromethane. The organic phase is washed with 10% strength aqueous sodium hydroxide solution, dried over sodium sulphate and reconcentrated under reduced pressure. This gives 6.9 g (86.7% of theory) of 4-chloro-6-(2-chlorophenoxy)-5-fluoropyrimidine.

$^1$H-NMR: δ=7.24–7.53 (m, 4H); 8.29 (s, 1H) ppm

EXAMPLE (IX-a-2)

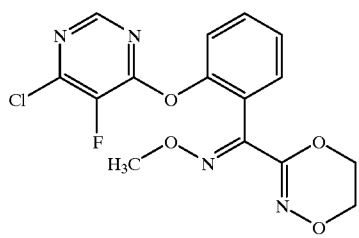

Process j)

To a mixture of 3 g (0.018 mol) of 4,6-dichloro-5-fluoropyrimidine and 2.7 g (0.018 mol) of potassium carbonate in 30 ml of acetonitrile is heated to 70° C. At this temperature, a solution of 3.8 g (0.03 mol) of (5,6-dihydro-[1.4.2]dioxazin-3-yl)-(2-hydroxy-phenyl)-methanone O-methyl oxime in 20 ml of acetonitrile is added dropwise over a period of 2 hours, and the mixture is heated under reflux for a further 16 hours. After cooling, the solvent is distilled off under reduced pressure and the residue is taken up in water and extracted repeatedly with in each case 40 ml of dichloromethane. The organic phase is washed with 10% strength aqueous sodium hydroxide solution, dried over sodium sulphate and reconcentrated under reduced pressure. This gives 7 g (86.7% of theory) of [2-(6-chloro-5-fluoropyrimidine-4-yloxy)-phenyl]-(5,6-dihydro-[1.4.2]-dioxazin-3-yl)-methanone O-methyl oxime.

$^1$H-NMR: δ=3.83 (s, 3H); 4.14 (m, 2H); 4.45 (m, 2H); 7.39–7.54 (m, 4H); 8.32 (s, 1H) ppm Preparation of 4,6-dichloro-5-fluoropyrimidine

EXAMPLE (XIII)

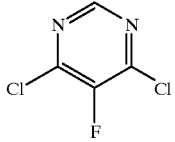

Process k)

Over a period of 30 minutes, 7.8 g (0.064 mol) of N,N-dimethylaniline are added dropwise to 30 ml of phosphorus oxychloride, and the mixture is stirred at 25° C. for 10 minutes. 8.3 g of 5-fluoropyrimidine-4,6-diole are subsequently added, and the mixture is heated under reflux for 15 hours. After cooling, the excess phosphorus oxychloride is distilled off under water pump vacuum and the residue is subjected to vacuum distillation. This gives 11.2 g (100% of theory) of 4,6-dichloro-5-fluoropyrimidine of boiling point 58–60° C. at 14 mbar.

Preparation of Compounds of the Formula (VII-a)

EXAMPLE (VII-a-1)

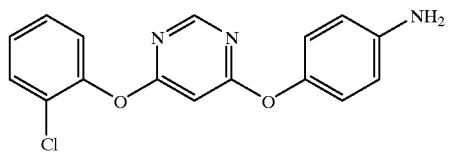

Process i)

A mixture of 2 g (9 mmol) of 4-(4-aminophenoxy)-6-chloro-pyrimidine, 1.1 g (9 mmol) of 3-chlorophenol and 2 g (18 mmol) of dried potassium carbonate in 20 ml of acetonitrile is heated under reflux for 4 hours. The mixture is subsequently filtered and the filtrate is concentrated under reduced pressure. The residue is taken up in dichloromethane, washed with water, and the organic phase is dried over sodium sulphate and reconcentrated under reduced pressure. This gives 1.3 g (46% of theory) of 4-(4-aminophenoxy)-6-(2-chlorophenoxy)-pyrimidine.

HPLC: log P=1.96

Preparation of Compounds of the Formula (XI)

EXAMPLE (XI-1)

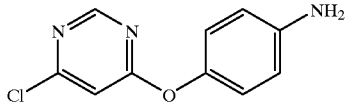

Process l

A mixture of 50 g (0.3 mol) of 4,6-dichloropyrimidine, 37 g (0.3 mol) of 4-aminophenol, 80 g (0.6 mol) of dried potassium carbonate and 50 mg of copper-II bromide in 600 ml of acetonitrile is heated under reflux for 4 hours. The mixture is subsequently filtered and the filtrate is concentrated under reduced pressure. The residue is taken up in dichloromethane, washed with water, and the organic phase is dried over sodium sulphate and reconcentrated under reduced pressure. This gives 60 g (58% of theory) of 4-(4-aminophenoxy)-6-chloro-pyrimidine.

HPLC: log P=0.65

EXAMPLE (VII-a-2)

Process h)

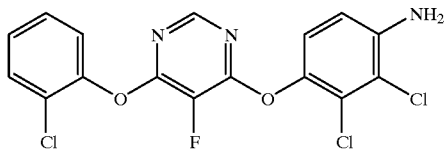

2.7 g of 6-chloro-5-fluoro-4-(2-chlorophenyloxy)pyrimidine and 1.5 g of potassium carbonate are initially charged in 20 ml of acetonitrile and, under reflux, admixed with 1.8 g of 2,3-dichloro-aminophenol over a period of 1.5 hours. The mixture is heated under reflux for a further 12 hours, cooled, the solvent is removed under reduced pressure and the residue is taken up in 45 ml of dichloromethane. The solution is washed with 0.25 N of aqueous sodium hydroxide solution and then admixed with 5 g of activated carbon and filtered, and the solvent is distilled off. The residue is chromatographed over silica gel using petroleum ether/ethyl acetate (2:1). This gives 2.7 g (64.3%) of 2,3-dichloro-4-[6-(2-chlorophenoxy)-5-fluoropyrimidin-4-yloxy]-phenylamine of melting point 162–163° C.

The compounds of the formula (I-f) mentioned in Table 5 below were obtained by the method of Example 1, and in accordance with the general description of the processes b) and c) according to the invention:

(I-f)

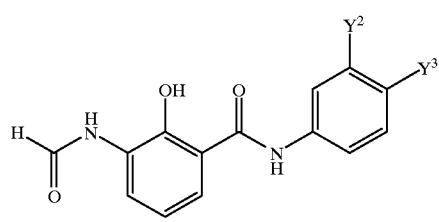

TABLE 5

| Example | $Y^2$ | $Y^3$ | logP |
|---|---|---|---|
| 2 | —H | 6-methoxy-pyrimidin-4-yloxy-phenyl | 2.96 |
| 3 | —H | 5-methoxy-3-phenyl-1,2,4-thiadiazole | 3.62 |
| 4 | —H | 6-methoxy-5-fluoro-4-(2-chlorophenoxy)pyrimidine | 3.61 |
| 5 | —CH$_3$ | 6-methoxy-5-fluoro-4-phenoxy-pyrimidine | 3.35 |
| 6 | —H | 6-methoxy-4-(2-fluorophenoxy)pyrimidine | 3.07 |
| 7 | —H | 6-methoxy-4-(2-chlorophenoxy)pyrimidine | 3.26 |
| 8 | —H | 6-methoxy-4-(4-trifluoromethylphenoxy)pyrimidine | 3.21 |
| 9 | —H | 6-methoxy-4-(3-chlorophenoxy)pyrimidine | 3.86 |
| 10 | —H | 6-methoxy-4-(3-fluorophenoxy)pyrimidine | 3.09 |
| 11 | —H | 6-methoxy-4-(3-trifluoromethylphenoxy)pyrimidine | 3.58 |
| 12 | —H | 6-methoxy-4-(3,4-difluorophenoxy)pyrimidine | 3.19 |
| 13 | —H | 6-methoxy-4-(4-bromophenoxy)pyrimidine | 3.53 |
| 14 | —H | 6-methoxy-4-(2,4-dichlorophenoxy)pyrimidine | 3.86 |
| 15 | —H | 6-methoxy-4-(3-methoxyphenoxy)pyrimidine | 2.95 |

TABLE 5-continued
| Example | $Y^2$ | $Y^3$ | logP |
|---|---|---|---|
| 16 | —H | 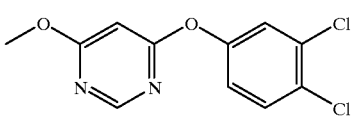 | 3.86 |
| 17 | —H | 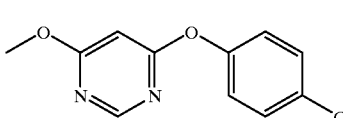 | 3.39 |
| 18 | —H | 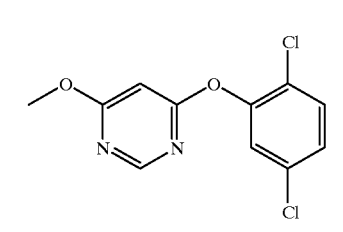 | 3.79 |
| 19 | —H | 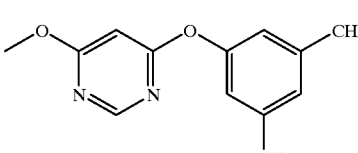 | 3.61 |
| 20 | —H | 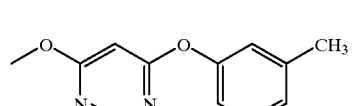 | 3.27 |
| 21 | —H | 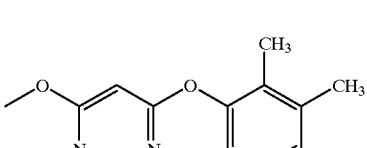 | 3.59 |
| 22 | —H | 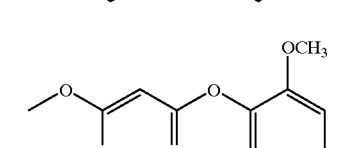 | 2.82 |
| 23 | —H | 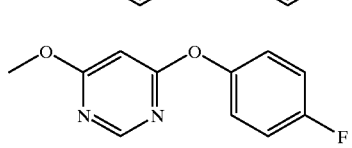 | 3.00 |
| 24 | —H | 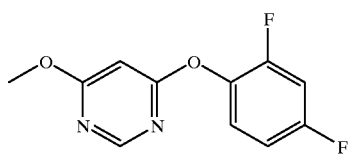 | 3.17 |
| 25 | —H | 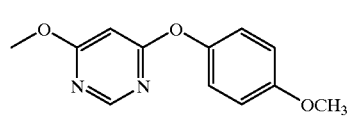 | 2.88 |
TABLE 5-continued
| Example | $Y^2$ | $Y^3$ | logP |
|---|---|---|---|
| 26 | —H | 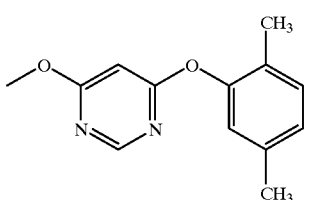 | 3.55 |
| 27 | —H | 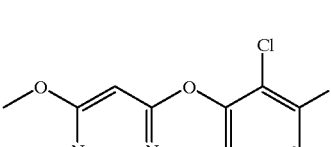 | 4.09 |
| 28 | —H | 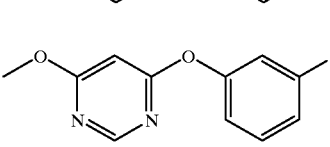 | 3.58 |
| 29 | —H | 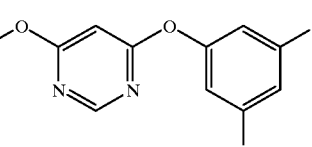 | 4.10 |
| 30 | —H | 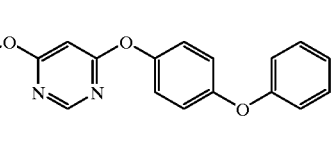 | 3.88 |
| 31 | —H | 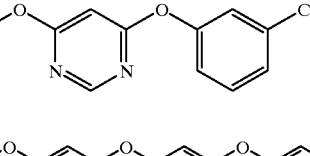 | 3.20 |
| 32 | —H | 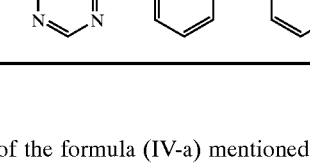 | 3.90 |
The compound of the formula (IV-a) mentioned in Table 6 below were obtained by the method of Example (IV-1), and in accordance with the general description of the process f) according to the invention:
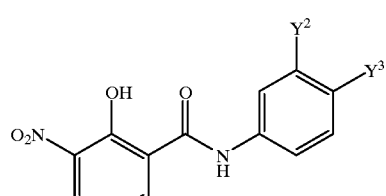
(IV-a)

TABLE 6

| Example | Y² | Y³ | phys. data |
|---|---|---|---|
| (IV-2) | —H | (4-methoxy-6-phenoxypyrimidine structure) | MS*: m/e = 444 (M⁺) |

*mass spectrum

The compounds of the formula (VI-a) mentioned in Table 7 below were obtained by the method of Example (V-1), and in accordance with the general description of the process g) according to the invention:

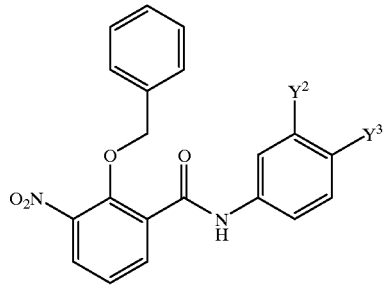

(V-a)

TABLE 7

| Example | Y² | Y³ | logP |
|---|---|---|---|
| (V-2) | —H | (6-methoxy-4-phenoxypyrimidine) | 4.24 |
| (V-3) | —H | (5-fluoro-6-methoxy-4-(2-chlorophenoxy)pyrimidine) | 4.83 |
| (V-4) | —H | (5-methoxy-3-(4-bromophenyl)-1,2,4-thiadiazole) | 5.75 |
| (V-5) | —H | (5-methoxy-3-phenyl-1,2,4-thiadiazole) | 4.99 |
| (V-6) | —H | (4-chloro-6-methoxypyrimidine) | 3.77 |

TABLE 7-continued

| Example | Y² | Y³ | logP |
|---|---|---|---|
| (V-7) | —CH₃ | (4-methoxy-6-phenoxy-2-fluoropyrimidine) | 4.65 |
| (V-8) | —H | (6-methoxy-4-(2-fluorophenoxy)pyrimidine) | 4.33 |
| (V-9) | —H | (6-methoxy-4-(2-chlorophenoxy)pyrimidine) | 4.55 |
| (V-10) | —H | (6-methoxy-4-(4-trifluoromethylphenoxy)pyrimidine) | 4.55 |
| (V-11) | —H | (6-methoxy-4-(3-chlorophenoxy)pyrimidine) | 4.73 |
| (V-12) | —H | (6-methoxy-4-(3-fluorophenoxy)pyrimidine) | 4.35 |
| (V-13) | —H | (6-methoxy-4-(3-trifluoromethylphenoxy)pyrimidine) | 4.79 |
| (V-14) | —H | (6-methoxy-4-(3,4-difluorophenoxy)pyrimidine) | 4.42 |
| (V-15) | —H | (6-methoxy-4-(4-bromophenoxy)pyrimidine) | 4.80 |
| (V-16) | —H | (6-methoxy-4-(2,4-dichlorophenoxy)pyrimidine) | 5.12 |

TABLE 7-continued
| Example | Y² | Y³ | logP |
|---|---|---|---|
| (V-17) | —H | 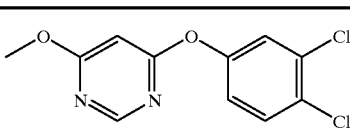 | 5.05 |
| (V-18) | —H | 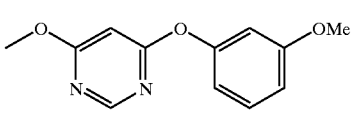 | 4.21 |
| (V-19) | —H | 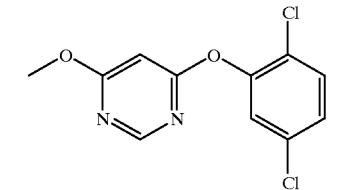 | 5.05 |
| (V-20) | —H | 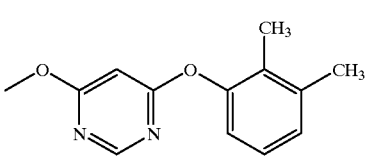 | 4.77 |
| (V-21) | —H | 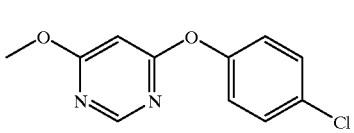 | 4.69 |
| (V-22) | —H | 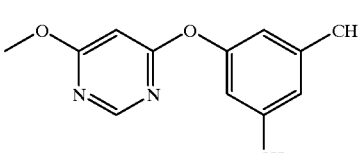 | 4.90 |
| (V-23) | —H | 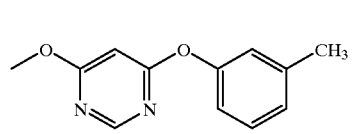 | 4.56 |
| (V-24) | —H | 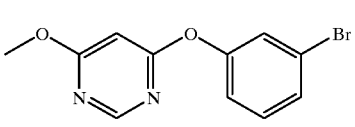 | 4.84 |
| (V-25) | —H | 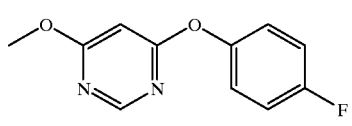 | 4.28 |
| (V-26) | —H | 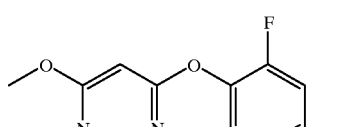 | 4.42 |
| (V-27) | —H | 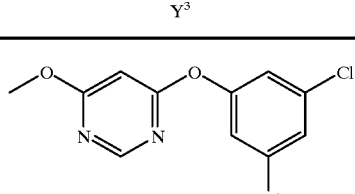 | 5.39 |
| (V-28) | —H | 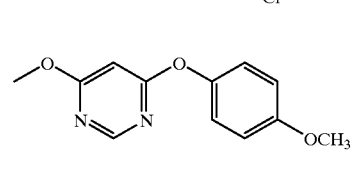 | 4.15 |
| (V-29) | —H | | 4.85 |
| (V-30) | —H | | 4.96 |
| (V-31) | —H | | 5.06 |
| (V-32) | —H | | 4.52 |
| (V-33) | —H | | 4.09 |
| (V-34) | —H | | 5.12 |
The compounds of the formula (VII-b) mentioned in Table 8 below were obtained by the methods of Examples (VII-a-1) and (VII-a-2), and in accordance with the general description of the processes h) and i) according to the invention:

TABLE 8
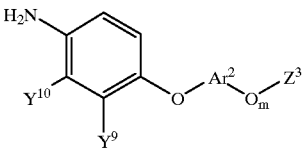
(VII-b)
| Ex. No. | Y¹⁰ | Y⁹ | Ar² | m | Z³ | m.p.: | LogP |
|---|---|---|---|---|---|---|---|
| VII-a-3 | —H | —H | 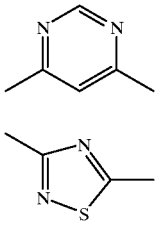 | 1 | phenyl | 130 | 1.53 |
| VII-a-4 | —H | —H | 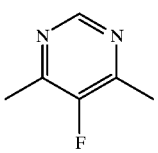 | 0 | phenyl |  | 2.57 |
| VII-a-5 | —H | —H | 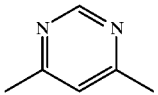 | 1 | phenyl |  | 1.88 |
| VII-a-6 | — | —CH3 | 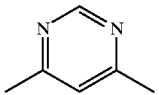 | 1 | phenyl |  | 2.32 |
| VII-a-7 | —H | —H | 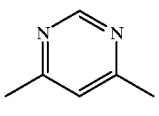 | 1 | 4-chloro-phenyl |  | 2.12 |
| VII-a-8 | —H | —H | 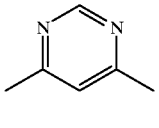 | 1 | 3,4-difluoro-phenyl |  | 4.55 |
| VII-a-9 | —H | —H | 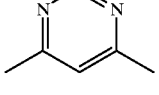 | 1 | 4-bromo-phenyl |  | 2.02 |
| VII-a-10 | —H | —H | 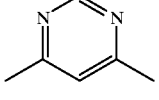 | 1 | 2,4-dichloro-phenyl |  | 2.33 |
| VII-a-11 | —H | —H | 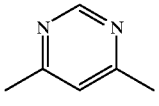 | 1 | 3,4-dichloro-phenyl |  | 2.48 |
| VII-a-12 | —H | —H | 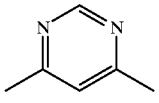 | 1 | 3-methoxy-phenyl |  | 1.61 |
| VII-a-13 | —H | —H |  | 1 | 4-tri-fluoromethyl-phenyl |  | 2.21 |

TABLE 8-continued (VII-b)

| Ex. No. | Y¹⁰ | Y⁹ | Ar² | m | Z³ | m.p.: | LogP |
|---|---|---|---|---|---|---|---|
| VII-a-14 | —H | —H | pyrimidine-4,6-diyl | 1 | 3-trifluoromethyl-phenyl | | 2.18 |
| VII-a-15 | —H | —H | pyrimidine-4,6-diyl | 1 | 2-fluoro-phenyl | | 1.61 |
| VII-a-16 | —H | —H | pyrimidine-4,6-diyl | 1 | 3-fluoro-phenyl | | 1.46 |
| VII-a-17 | —H | —H | pyrimidine-4,6-diyl | 1 | 3-tolyl | | 2.12 |
| VII-a-18 | —H | —H | pyrimidine-4,6-diyl | 1 | 2,5-dichloro-phenyl | | 2.26 |
| VII-a-19 | —H | —H | pyrimidine-4,6-diyl | 1 | 2,3-dimethyl-phenyl | | 1.98 |
| VII-a-20 | —H | —H | pyrimidine-4,6-diyl | 1 | 3,5-dimethyl-phenyl | | 2.12 |
| VII-a-21 | —H | —H | pyrimidine-4,6-diyl | 1 | 2,4-difluoro-phenyl | | 1.76 |
| VII-a-22 | —H | —H | pyrimidine-4,6-diyl | 1 | 3,5-dichloro-phenyl | | 2.6 |
| VII-a-23 | —H | —H | pyrimidine-4,6-diyl | 1 | 4-methoxy-phenyl | | 1.52 |
| VII-a-24 | —H | —H | pyrimidine-4,6-diyl | 1 | 4-fluoro-phenyl | | 1.59 |

TABLE 8-continued (VII-b)

$$\text{H}_2\text{N} - \text{C}_6\text{H}_2(\text{Y}^{10})(\text{Y}^9) - \text{O} - \text{Ar}^2 - \text{O}_m - \text{Z}^3$$

| Ex. No. | Y¹⁰ | Y⁹ | Ar² | m | Z³ | m.p.: | LogP |
|---------|-----|-----|-----|---|-----|-------|------|
| VII-a-25 | —H | —H | 4,6-dimethylpyrimidin-5-yl | 1 | 3-bromo-phenyl | | 2.05 |
| VII-a-26 | —H | —H | 4,6-dimethylpyrimidin-5-yl | 1 | 2,3-dichloro-phenyl | | 2.26 |
| VII-a-27 | —H | —H | 4,6-dimethylpyrimidin-5-yl | 1 | 2,5-dimethyl-phenyl | | 2.02 |
| VII-a-28 | —H | —H | 4,6-dimethylpyrimidin-5-yl | 1 | 4-phenoxy-phenyl | | 2.55 |
| VII-a-29 | —H | —H | 4,6-dimethylpyrimidin-5-yl | 1 | 2-methoxy-phenyl | | 1.46 |
| VII-a-30 | —H | —H | 4,6-dimethylpyrimidin-5-yl | 1 | 2-tolyl | | 1.71 |
| VII-a-31 | —H | —H | 4,6-dimethylpyrimidin-5-yl | 1 | 3-phenoxy-phenyl | | 2.54 |
| VII-a-32 | —H | —H | 4,6-dimethyl-5-fluoropyrimidin-5-yl | 1 | 2-chloro-phenyl | | 3.61 |
| VII-a-33 | —H | —H | 4,6-dimethylpyrimidin-5-yl | 1 | 2,6-dimethyl-phenyl | | |
| VII-a-34 | —H | —H | 4,6-dimethylpyrimidin-5-yl | 1 | 2,6-dichloro-phenyl | | |

Use Examples

EXAMPLE A

Phytophthora test (tomato)/protective
Solvent: 47 parts by weight of acetone
Emulsifier: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of Phytophthora infestans. The plants are then placed in an incubation cabin at approximately 20° C. and 100% relative atmospheric humidity.

Evaluation is carried out 3 days after the inoculation. 0% means an efficacy which corresponds to that of the control, whereas an efficacy of 100% means that no infection is observed.

In this test, for example, the following compounds of Preparation Examples 1, 2 and 4 exhibit, at an exemplary active compound application rate of 100 g/ha, an efficacy of more than 80%, compared with the untreated control.

EXAMPLE B

Venturia test (apple)/protective
Solvent: 47 parts by weight of acetone
Emulsifier: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the causative organism of apple scab Venturia inaequalis and then remain in an incubation cabin at approximately 20° C. and 100% relative atmospheric humidity for 1 day.

The plants are then placed in a greenhouse at approximately 21° C. and a relative atmospheric humidity of approximately 90%.

Evaluation is carried out 12 days after the evaluation. 0% means an efficacy which corresponds to that of the control, whereas an efficacy of 100% means that no infection is observed.

In this test, for example, the following compounds of Preparation Examples 1 and 2 exhibit, at an exemplary active compound application rate of 100 g/ha, an efficacy of more than 80%, compared with the untreated control.

What is claimed is:

1. Compounds of the formula (I)

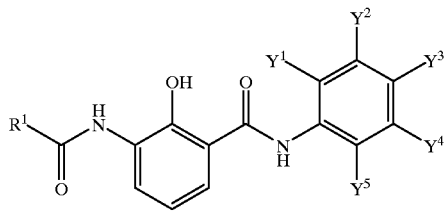

(I)

in which $R^1$ represents hydrogen, alkyl or alkoxy,
$Y^1$, $Y^2$, $Y^3$, $Y^4$ and $Y^5$ are identical or different and each represents hydrogen, halogen, cyano, alkyl, halogenoalkyl, alkoxy or halogenoalkoxy, and either
$Y^2$ or $Y^3$ represents —G—Z, in which
G represents one of the groupings below
—Q—CQ—, —CQ—Q—, —CQ—Q—CH$_2$—,
—CH$_2$—Q—CQ—, —Q—CQ—CH$_2$—,
—Q—CQ—Q—CH$_2$—, —N▽N—, S(O)$_n$—,
—CH$_2$—S(O)$_n$—, —CQ—, —S(O)$_n$—CH$_2$—,
—C(R$^3$)=N—O—, —C(R$^3$)=N—O—CH$_2$—,
—N(R$^4$)—, —CQ—N(R$^4$)—, —N(R$^4$)—CQ—,
—Q—CQ—N(R$^4$)—, —N=C(R$^3$)—Q—CH$_2$—,
—CH$_2$—O—N=C(R$^3$)—, —C(CH$_3$)—O—N=C(R$^3$)—, —N(R$^4$)—CQ—Q—, —CQ—N(R$^4$)—CQ—Q—, —N(R$^4$)—CQ—Q—CH$_2$—, —Q—C(R$^3$)=N—O—CH$_2$—, —N(R$^4$)—C(R$^3$)=N—O—CH$_2$—, —O—CH$_2$—C(R$^3$)=N—O—CH$_2$—,
—N=N—C(R$^3$)=N—O—CH$_2$—, —C(=N—O—R$^5$)—C(R$^3$)=N—O—CH$_2$—, —C(=N—O—R$^5$)—C(R$^3$)—O—N=CH—, —C(=N—O—R$^5$)—C(R$^3$)—O—N=C(CH$_3$)—, —T—Ar$^1$— or —T—Ar$^1$—Q—, where
Ar$^1$ represents optionally substituted arylene, heteroarylene, cycloalkylene or heterocycloalkylene (i.e. a doubly attached aliphatic ring in which one or more carbon atoms are replaced by heteroatoms, i.e. by atoms different from carbon),
n represents the numbers 0, 1 or 2,
Q represents oxygen or sulphur,
R$^3$ represents hydrogen, cyano or in each case optionally substituted alkyl, alkoxy, alkylthio, alkylamino, dialkylamino or cycloalkyl, and
R$^4$ represents hydrogen, hydroxyl, cyano or in each case optionally substituted alkyl, alkoxy or cycloalkyl,
R$^5$ represents hydrogen or alkyl and
T represents a single bond, represents oxygen, sulphur, —CH$_2$—O—, —CH$_2$—S— or represents optionally substituted alkanediyl,
Z represents in each case optionally substituted alkyl, alkenyl, alkinyl, cycloalkyl, aryl or heterocyclyl.

2. Compounds of the formula (I) according to claim 1, in which
R$^1$ represents hydrogen, alkyl having 1 to 4 carbon atoms or alkoxy having 1 to 4 carbon atoms,
$Y^1$, $Y^2$, $Y^3$, $Y^4$ and $Y^5$ are identical or different and each represents hydrogen, halogen, cyano, alkyl or alkoxy having in each case 1 to 4 carbon atoms, halogenoalkyl, or halogenoalkoxy having in each case 1 to 4 carbon atoms and 1 to 5 identical or different halogen atoms, and either
$Y^2$ or $Y^3$ represents —G—Z, in which
G represents one of the groupings below
—Q—CQ—, —CQ—Q—, —CQ—Q—CH$_2$—,
—CH$_2$—Q—CQ—, —Q—CQ—CH$_2$—,
—Q—CQ—Q—CH$_2$—, —N=N—, —S(O)$_n$—,
—CH$_2$—S(O)$_n$—, —CQ—, —S(O)$_n$—CH$_2$—,
—C(R$^3$)=N—O—, —C(R$^3$)=N—O—CH$_2$—,
—N(R$^4$)—, —CQ—N(R$^4$)—, —N(R$^4$)—CQ—,
—Q—CQ—N(R$^4$)—, —N=C(R$^3$)—Q—CH$_2$—,
—CH$_2$—O—N=C(R$^3$)—, —C(CH$_3$)—O—N=C(R$^3$)—, —N(R$^4$)—CQ—Q—, —CQ—N(R$^4$)—CQ—Q—, —N(R$^4$)—CQ—Q—CH$_2$—, —Q—C(R$^3$)=N—O—CH$_2$—, —N(R$^4$)—C(R$^3$)=N—O—CH$_2$—, —O—CH$_2$—C(R$^3$)=N—O—CH$_2$—, —N=N—C(R³)=N—O—CH₂—, —C(=N—O—R⁵)—C(R³)=N—O—CH₂—, —C(=N—O—R⁵)—C(R³)—O—N=CH—, —C(=N—O—R⁵)—C(R³)—O—N=C(CH₃)—, —T—Ar¹— or —T—Ar¹—Q—, where n represents the numbers 0, 1 or 2, Q represents oxygen or sulphur, R³ represents hydrogen, cyano, represents in each case optionally halogen-, cyano- or $C_1$–$C_4$-alkoxy-substituted alkyl, alkoxy, alkylthio, alkylamino or dialkylamino having in each case 1 to 6 carbon atoms in the alkyl groups or represents in each case optionally halogen-, cyano-, carboxyl-, $C_1$–$C_4$-alkyl- or $C_1$–$C_4$-alkoxycarbonyl-substituted cycloalkyl having 3 to 6 carbon atoms, and R⁴ represents hydrogen, hydroxyl, cyano or represents optionally halogen-, cyano- or $C_1$–$C_4$-alkoxy-substituted alkyl having 1 to 6 carbon atoms or represents optionally halogen-, cyano-, carboxyl-, $C_1$–$C_4$-alkyl- or $C_1$–$C_4$-alkoxy-carbonyl-substituted cycloalkyl having 3 to 6 carbon atoms, R⁵ represents hydrogen or alkyl having 1 to 4 carbon atoms, Ar¹ represents phenylene, naphthylene or cycloalkylene, each of which is optionally mono- or polysubstituted by identical or different substituents, or represents heteroarylene or heterocycloalkylene having 3 to 7 ring members, at least one of which represents oxygen, sulphur or nitrogen and one or two more optionally represent nitrogen, where the possible substituents are preferably selected from the list below:

halogen, cyano, amino, hydroxyl, formyl, carboxyl, carbamoyl, thiocarbamoyl;

in each case straight-chain or branched alkyl, alkoxy, alkylthio, alkylsulphinyl or alkylsulphonyl having in each case 1 to 6 carbon atoms;

in each case straight-chain or branched alkenyl or alkenyloxy having in each case 2 to 6 carbon atoms;

in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 11 identical or different halogen atoms;

in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties, and also cycloalkyl having 3 to 6 carbon atoms and T represents a single bond, represents oxygen, sulphur, —CH₂—O—, —CH₂—S— or represents alkanediyl having 1 to 3 carbon atoms, Z represents alkyl having 1 to 8 carbon atoms which is optionally mono- or polysubstituted by identical or different substituents selected from the group consisting of halogen, cyano, hydroxyl, amino, $C_1$–$C_4$-alkoxy, $C_1$–$C_4$-alkylthio, $C_1$–$C_4$-alkylsulphinyl and $C_1$–$C_4$-alkylsulphonyl (each of which may optionally be substituted by halogen);

represents in each case optionally halogen-substituted alkenyl or alkinyl having in each case up to 8 carbon atoms;

represents cycloalkyl having 3 to 6 carbon atoms which is in each case optionally mono- or polysubstituted by identical or different substituents selected from the group consisting of halogen, cyano, carboxyl, phenyl (which is optionally substituted by halogen, cyano, $C_1$–$C_4$-alkyl, $C_1$–$C_4$-halogenoalkyl, $C_1$–$C_4$-alkoxy or $C_1$–$C_4$-halogenoalkoxy), $C_1$–$C_4$-alkyl and $C_1$–$C_4$-alkoxy-carbonyl;

represents phenyl, naphthyl, each of which is optionally mono- or polysubstituted by identical or different substituents, or represents heterocyclyl having 3 to 7 ring members, at least one of which represents oxygen, sulphur or nitrogen and one or two more optionally represent nitrogen, where the possible substituents are preferably selected from the list below:

halogen, cyano, amino, hydroxyl, formyl, carboxyl, carbamoyl, thiocarbamoyl;

in each case straight-chain or branched alkyl, alkoxy, alkylthio, alkylsulphinyl or alkylsulphonyl having in each case 1 to 6 carbon atoms;

in each case straight-chain or branched alkenyl or alkenyloxy having in each case 2 to 6 carbon atoms;

in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 11 identical or different halogen atoms;

in each case straight-chain or branched alkylamino, dialkylamino, alkylcarbonyl, alkylcarbonyloxy, alkoxycarbonyl or alkylsulphonyloxy, having in each case 1 to 6 carbon atoms in the individual alkyl moieties;

in each case doubly attached alkylene or dioxyalkylene having in each case 1 to 6 carbon atoms and being in each case optionally mono- or polysubstituted by identical or different substituents selected from the group consisting of halogen, straight-chain or branched alkyl having 1 to 4 carbon atoms and straight-chain or branched halogenoalkyl having 1 to 4 carbon atoms and 1 to 9 identical or different halogen atoms;

cycloalkyl having 3 to 6 carbon atoms;

phenyl or phenoxy, each of which is mono- or polysubstituted by identical or different substituents selected from the group consisting of halogen and straight-chain or branched alkyl having 1 to 4 carbon atoms;

heterocyclyl or heterocyclyl-methyl having in each case 3 to 7 ring members, 1 to 3 of which are in each case identical or different heteroatoms—in particular nitrogen, oxygen and/or sulphur-, or a grouping 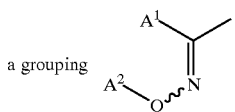

in which
A¹ represents alkyl having 1 to 4 carbon atoms or cycloalkyl having 1 to 6 carbon atoms and
A² represents optionally cyano-, alkoxy-, alkylthio-, alkylamino-, dialkylamino- or phenyl-substituted alkyl having 1 to 4 carbon atoms, alkenyl or alkinyl having in each case 2 to 4 carbon atoms, or a grouping 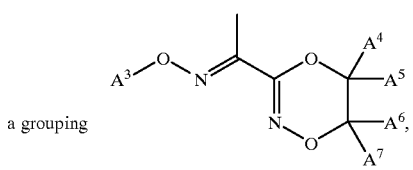

in which
A³ represents alkyl having 1 to 4 carbon atoms and
A⁴, A⁵, A⁶ and A⁷ are identical or different and, independently of one another, each represents hydrogen, alkyl or hydroxyalkyl having in each case 1 to 4 carbon atoms or halogenoalkyl having 1 to 4 carbon atoms and 1 to five identical or different halogen atoms, or
A⁴ and A⁵ or A⁴ and A⁶ or A⁶ and A⁷ together with the respective carbon atoms to which they are attached form a cycloaliphatic ring having five, six or seven carbon atoms.

3. Compounds of the formula (I) according to claim 1, in which
R¹ represents hydrogen, methyl, ethyl, n- or i-propyl, methoxy or ethoxy,
Y¹, Y², Y³, Y⁴ and Y⁵ are identical or different and each represents hydrogen, fluorine, chlorine, bromine, cyano, methyl, ethyl, methoxy, trifluoromethyl or difluoromethoxy, and either
Y² or Y³ represents —G—Z, in which
G represents one of the groupings below
—Q—CQ—, —CQ—Q—, —CQ—Q—CH₂—, —CH₂—Q—CQ—, —Q—CQ—CH₂—, —Q—CQ—Q—CH₂—, —N═N—, —S(O)ₙ—, —CH₂—S(O)ₙ—, —CQ—, —S(O)ₙ—CH₂—, —C(R³)═N—O—, —C(R³)═N—O—CH₂—, —N(R⁴)—, —CQ—N(R⁴)—, —N(R⁴)—CQ—, —Q—CQ—N(R⁴)—, —N═C(R³)—Q—CH₂—, —CH₂—O—N═C(R³)—, —C(CH₃)—O—N═C(R³)—, —N(R⁴)—CQ—Q—, —CQ—N(R⁴)—CQ—Q—, —N(R⁴)—CQ—Q—CH₂—, —Q—C(R³)═N—O—CH₂—, —N(R⁴)—C(R³)═N—O—CH₂—, —O—CH₂—C(R³)═N—O—CH₂—, —N═N—C(R³)═N—O—CH₂—, —C(═N—O—R⁵)—C(R³)═N—O—CH₂—, —C(═N—O—R⁵)—C(R³)—O—N═CH—, —C(═N—O—R⁵)—C(R³)—O—N═C(CH₃)—, —T—Ar¹— or —T—Ar¹—Q—, where
n represents the numbers 0, 1 or 2,
Q represents oxygen or sulphur,
R³ represents hydrogen, cyano, methyl, ethyl or cyclopropyl and R⁴ represents hydrogen, methyl, ethyl or cyclopropyl,
R⁵ represents hydrogen or methyl,
Ar¹ represents phenylene or pyridinediyl, each of which is optionally mono- to trisubstituted by identical or different substituents, represents in each case optionally monosubstituted pyrimidinediyl, pyridazinediyl, pyrazinediyl, 1,2,3-triazinediyl, 1,2,4-triazinediyl or 1,3,5-triazinediyl or represents 1,2,4-thiadiazolediyl, 1,3,4-thiadiazolediyl, 1,2,4-oxadiazolediyl, 1,3,4-oxadiazolediyl, where the possible substituents are preferably selected from the list below:
fluorine, chlorine, bromine, cyano, methyl, ethyl, n- or i-propyl, cyclopropyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl and
T represents a single bond, represents oxygen, sulphur, —CH₂—O—, CH₂—S—, methylene, ethylene or propylene,
Z represents ethyl, n- or i-propyl, n-, i-, s- or t-butyl or methyl which is optionally mono- to trisubstituted by identical or different substituents selected from the group consisting of fluorine, chlorine, cyano and methoxy;
represents in each case optionally fluorine- or chlorine-substituted vinyl, allyl or propargyl;
represents cyclopropyl, cyclobutyl, cyclopentyl or cyclohexyl, each of which is optionally mono- to trisubstituted by identical or different substituents selected from the group consisting of fluorine, chlorine, cyano, methoxy, phenyl, methyl or ethyl; or
Z represents phenyl, 1,2,4-thiadiazolyl, 1,3,4-thiadiazolyl, 1,2,4-oxadiazolyl, 1,3,4-oxadiazolyl, pyridinyl, pyrimidyl, pyridazinyl, pyrazinyl, 1,2,3-triazinyl, 1,2,4-triazinyl or 1,3,5-triazinyl, each of which is optionally mono- to trisubstituted by identical or different substituents, where the possible substituents are preferably selected from the list below:
fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl,
in each case doubly attached methylenedioxy, ethylenedioxy, each of which is optionally mono- to tetrasubstituted by identical or different substituents selected from the group consisting of fluorine, chlorine, methyl, trifluoromethyl or ethyl,
phenyl, 4-chlorophenyl, 4-methylphenyl, phenoxy, 4-chlorophenoxy, 4-methylphenoxy, cyclopropyl, cyclobutyl, cyclopentyl or cyclohexyl, or a grouping 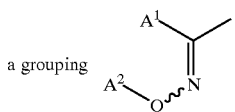, in which A¹ represents methyl, ethyl, n- or i-propyl, n-, i-, s- or t-butyl, cyclopropyl or cyclobutyl, A² represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl, or a grouping 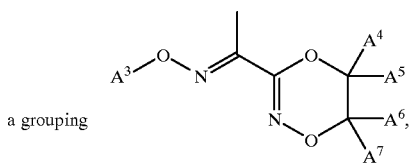

in which

A³ represents methyl or ethyl and

A⁴, A⁵, A⁶ and A⁷ are identical or different and independently of one another each represents hydrogen, methyl, ethyl, n- or i-propyl, n-, i-, s- or t-butyl, hydroxymethyl, trifluoromethyl or trifluoroethyl, or A⁴ and A⁵ or A⁴ and A⁶ or A⁶ and A⁷ together with the respective carbon atoms to which they are attached form a cycloaliphatic ring having five, six or seven carbon atoms.

4. Compounds of the formula (I) according to claim 1, in which

R¹ represents hydrogen, methyl or methoxy,

Y¹, Y², Y³, Y⁴ and Y⁵ are identical or different and each represents hydrogen, fluorine, chlorine, bromine, cyano, methyl, ethyl, methoxy, trifluoromethyl or difluoromethoxy, and either Y² or Y³ represents —G—Z, in which G represents —C(R³)=N—O—CH₂—, in which R³ represents methyl or cyclopropyl, and Z represents phenyl, pyridyl or pyrimidyl, each of which is optionally mono- to trisubstituted by identical or different substituents, where the possible substituents are preferably selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, methoximinomethyl, ethoximinomethyl, methoximinoethyl, ethoximinoethyl, in each case doubly attached methylenedioxy or ethylenedioxy, each of which is optionally mono- to tetrasubstituted by identical or different substituents selected from the group consisting of fluorine, chlorine, methyl, trifluoromethyl and ethyl, and also phenyl and phenoxy.

5. Compounds of the formula (I) according to claim 1, in which

R¹ represents hydrogen, methyl or methoxy,

Y¹, Y², Y³, Y⁴ and Y⁵ are identical or different and each represents hydrogen, fluorine, chlorine, bromine, cyano, methyl, ethyl, methoxy, trifluoromethyl or difluoromethoxy, and either Y² or Y³ represents —G—Z, in which G represents —T—Ar¹— or —T—Ar¹—O—, in which Ar¹ represents 1,2,4-thiadiazolediyl, 1,3,4-thiadiazolediyl, 1,2,4-oxadiazolediyl, 1,3,4-oxadiazolediyl or represents pyridinediyl, pyrimidinediyl or 1,3,5-triazinediyl, each of which is optionally mono- or disubstituted by identical or different substituents selected from the group consisting of fluorine, chlorine, cyano, methyl, cyclopropyl, methoxy, methylthio, trifluoromethyl, difluoromethoxy, trifluoromethoxy, difluorochloromethoxy, T represents a single bond, represents oxygen, sulphur, —CH₂—O—, CH₂—S—, methylene, ethylene or propylene and Z represents methyl, ethyl, n- or i-propyl, n-, i-, s- or t-butyl, which is optionally mono- to trisubstituted by identical or different substituents selected from the group consisting of fluorine, chlorine, cyano or methoxy;

represents in each case optionally fluorine- or chlorine-substituted vinyl, allyl or propargyl;

represents cyclopropyl, cyclobutyl, cyclopentyl or cyclohexyl, each of which is optionally mono- to trisubstituted by identical or different substituents selected from the group consisting of fluorine, chlorine, cyano, methoxy, phenyl, methyl or ethyl; or Z represents phenyl, pyridyl, pyrimidyl or thienyl, each of which is optionally mono- to trisubstituted by identical or different substituents, where the possible substituents are preferably selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl, trifluoromethylsulphonyl, methoxycarbonyl, ethoxycarbonyl or phenoxy;

in each case doubly attached methylenedioxy, ethylenedioxy, each of which is optionally mono- to tetrasubstituted by identical or different substituents selected from the group consisting of fluorine, chlorine, methyl, trifluoromethyl and ethyl cyclopropyl, cyclobutyl, cyclopentyl, cyclohexyl, phenyl, phenoxy, or a grouping 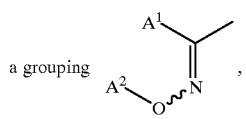, in which
A¹ represents methyl, ethyl, n- or i-propyl, n-, i-, s- or t-butyl, cyclopropyl or cyclobutyl,
A² represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl, or a grouping 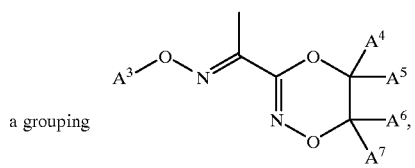

in which
A³ represents methyl or ethyl and
A⁴, A⁵, A⁶ and A⁷ are identical or different and independently of one another each represents hydrogen, methyl, ethyl, n- or i-propyl, n-, i-, s- or t-butyl, hydroxymethyl, trifluoromethyl or trifluoroethyl, or
A⁴ and A⁵ or A⁴ and A⁶ or A⁶ and A⁷ together with the respective carbon atoms to which they are attached form a cycloaliphatic ring having five, six or seven carbon atoms.

6. Compounds of the formula (IV),

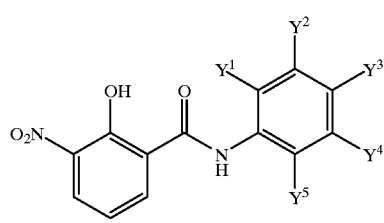

(IV)

in which
Y¹, Y², Y³, Y⁴ and Y⁵ are each as defined in claim 1.

7. A pesticide composition comprising at least one of the compounds of the formula (I) according to claim 1 and extenders and/or surfactants.

8. A method for controlling pests comprising applying compounds of the formula (I) according to claim 1 on pests and/or their habitat.

9. A process for preparing compounds of the formula (I),

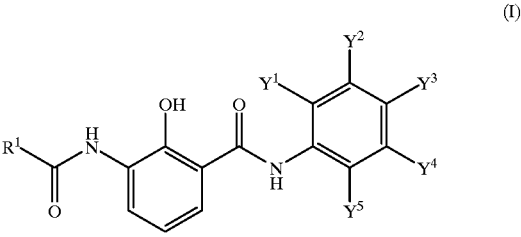

(I)

in which
$R^1$ represents hydrogen, alkyl or alkoxy,
$Y^1$, $Y^2$, $Y^3$, $Y^4$ and $Y^5$ are identical or different and each represents hydrogen, halogen, cyano, alkyl, halogenoalkyl, alkoxy or halogenoalkoxy, and either
$Y^2$ or $Y^3$ represents —G—Z, in which
G represents one of the groupings below
—Q—CQ—, —CQ—Q—, —CQ—Q—CH₂—, —CH₂—Q—CQ—, —Q—CQ—CH₂—, —Q—CQ—Q—CH₂—, —N=N—, —S(O)$_n$—, —CH₂—S(O)$_n$—, —CQ—, —S(O)$_n$—CH₂—, —C(R³)=N—O—, —C(R³)=N—O—CH₂—, —N(R⁴)—, —CQ—N(R⁴)—, —N(R⁴)—CQ—, —Q—CQ—N(R⁴)—, —N=C(R³)—Q—CH₂—, —CH₂—O—N=C(R³)—, —C(CH₃)—O—N=C(R³)—, —N(R⁴)—CQ—Q—, —CQ—N(R⁴)—CQ—Q—, —N(R⁴)—CQ—Q—CH₂—, —Q—C(R³)=N—O—CH₂—, —N(R⁴)—C(R³)=N—O—CH₂—, —O—CH₂—C(R³)=N—O—CH₂—, —N=N—C(R³)=N—O—CH₂—, —C(=N—O—R⁵)—C(R³)=N—O—CH₂—, —C(=N—O—R⁵)—C(R³)—O—N=CH—, —C(=N—O—R⁵)—C(R³)—O—N=C(CH₃)—, —T—Ar¹— or —T—Ar¹—Q—, where
Ar¹ represents optionally substituted arylene, heteroarylene, cycloalkylene or heterocycloalkylene (i.e. a doubly attached aliphatic ring in which one or more carbon atoms are replaced by heteroatoms, i.e. by atoms different from carbon),
n represents the numbers 0, 1 or 2,
Q represents oxygen or sulphur,
$R^3$ represents hydrogen, cyano or in each case optionally substituted alkyl, alkoxy, alkylthio, alkylamino, dialkylamino or cycloalkyl, and
$R^4$ represents hydrogen, hydroxyl, cyano or in each case optionally substituted alkyl, alkoxy or cycloalkyl,
$R^5$ represents hydrogen or alkyl and
T represents a single bond, represents oxygen, sulphur, —CH₂—O—, —CH₂—S— or represents optionally substituted alkanediyl,
Z represents in each case optionally substituted alkyl, alkenyl, alkinyl, cycloalkyl, aryl or heterocyclyl, comprising reacting a) aminosalicylamides of the general formula (II),

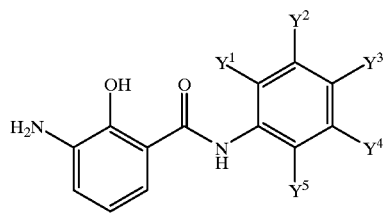

(II)

in which
Y$^1$, Y$^2$, Y$^3$, Y$^4$ and Y$^5$ are each as defined above, with acylating agents of the general formula (III),

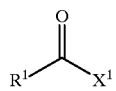

(III)

in which
R$^1$ is as defined above and
X$^1$ represents halogen, hydroxyl, alkoxy or alkylcarbonyloxy, if appropriate in the presence of a diluent, if appropriate in the presence of an acid acceptor, and if appropriate in the presence of a further reaction auxiliary, or reacting
b) nitrosalicylamides of the general formula (IV)

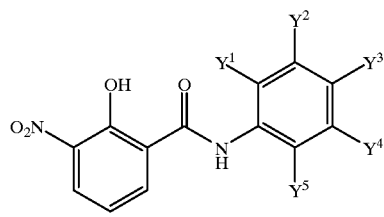

(IV)

in which
Y$^1$, Y$^2$, Y$^3$, Y$^4$ and Y$^5$ are each as defined above, with formic acid, if appropriate in the presence of a catalyst and if appropriate in the presence of a further reaction auxiliary, or reacting
c) O-benzyl-nitrosalicylamides of the general formula (V),

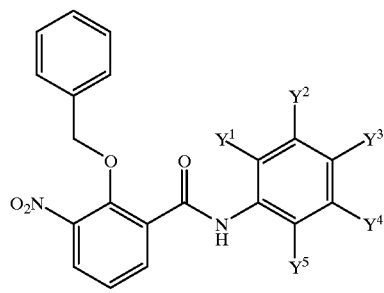

(V)

in which
Y$^1$, Y$^2$, Y$^3$, Y$^4$ and Y$^5$ are each as defined above, with formic acid, if appropriate in the presence of hydrogen or a base metal, if appropriate in the presence of a catalyst and if appropriate in the presence of a further reaction auxiliary.

10. A process for preparing compounds of the formula (IV) as defined in claim 6, comprising reacting 2-hydroxy-3-nitrobenzoic acid or 2-hydroxy-3-nitrobenzoyl chloride with an amine of the formula (VII)

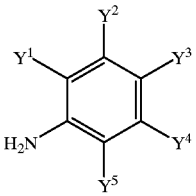

(VII)

in which
Y$^1$, Y$^2$, Y$^3$, Y$^4$ and Y$^5$ are each as defined above, if appropriate in the presence of a diluent, if appropriate in the presence of a condensing agent and if appropriate in the presence of an acid acceptor.

11. A process for preparing pesticides comprising mixing compounds of the formula (I) according to claim 1 with extenders and/or surfactants.

12. Compounds of the formula (II)

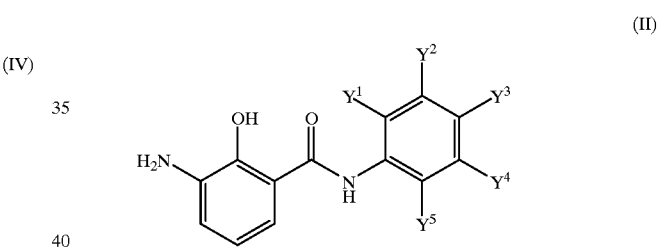

(II)

in which
Y$^1$, Y$^2$, Y$^3$, Y$^4$ and Y$^5$ are each as defined in claim 1.

13. A process for preparing compounds of the formula (II) as defined in claim 12 comprising reacting nitrosalicylamides of the general formula (IV)

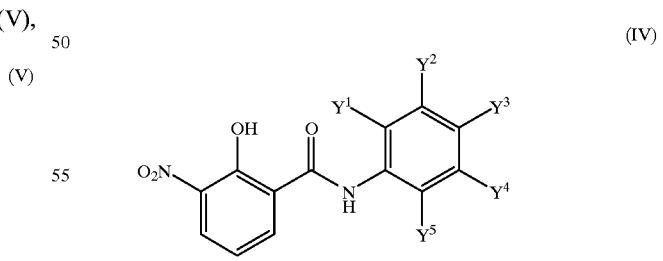

(IV)

in which
Y$^1$, Y$^2$, Y$^3$, Y$^4$ and Y$^5$ are each as defined above with a reducing agent, if appropriate in the presence of a diluent and if appropriate in the presence of a catalyst, or reacting O-benzyl-nitrosalicylamides of the general formula (V)

(V)

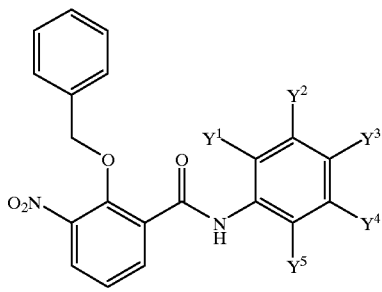

in which
Y¹, Y², Y³, Y⁴ and Y⁵ are each as defined above with hydrogen, if appropriate in the presence of a diluent and if appropriate in the presence of a catalyst.

14. Compounds of the formula (V), (V)

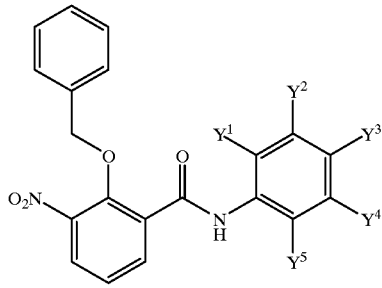

in which
Y¹, Y², Y³, Y⁴ and Y⁵ are each as defined in claim 1.

15. A process for preparing compounds of the formula (V) as defined in claim 14 comprising reacting O-benzyl-nitrosalicylic acid derivatives of the formula (VI)

(VI)

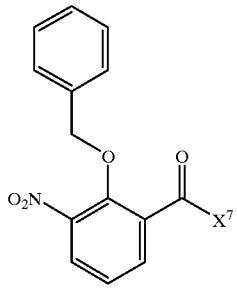

in which $X^7$ represents halogen, hydroxyl or alkoxy with an amine of the formula (VII), if appropriate in the presence of a diluent, if appropriate in the presence of a condensing agent and if appropriate in the presence of an acid acceptor.

16. A pesticide composition comprising at least one of the compounds of the formula (IV) according to claim 6 and extenders and/or surfactants.

17. A method for controlling pests comprising applying compounds of the formula (IV) according to claim 6 on pests and/or their habitat.

18. A process for preparing pesticides comprising mixing compounds of the formula (IV) according to claim 6 with extenders and/or surfactants.

* * * * *